US011497966B2

(12) United States Patent
Jung et al.

(10) Patent No.: US 11,497,966 B2
(45) Date of Patent: Nov. 15, 2022

(54) AUTOMATIC COACHING SYSTEM AND METHOD FOR COACHING USER'S EXERCISE

(71) Applicant: BEFLEX INC., Daejeon (KR)

(72) Inventors: Juho Jung, Daejeon (KR); Chang Keun Jung, Daejeon (KR); Seongjae Yoo, Daejeon (KR)

(73) Assignee: Beflex Inc., Daejeon (KR)

( * ) Notice: Subject to any disclaimer, the term of this patent is extended or adjusted under 35 U.S.C. 154(b) by 682 days.

(21) Appl. No.: 16/272,201

(22) Filed: Feb. 11, 2019

(65) Prior Publication Data
US 2019/0224529 A1    Jul. 25, 2019

Related U.S. Application Data

(63) Continuation-in-part of application No. PCT/KR2017/008533, filed on Aug. 8, 2017, which
(Continued)

(30) Foreign Application Priority Data

Aug. 9, 2016  (KR) .................. 10-2016-0101489
Aug. 9, 2016  (KR) .................. 10-2016-0181491
(Continued)

(51) Int. Cl.
G06F 3/048    (2013.01)
A63B 24/00   (2006.01)
(Continued)

(52) U.S. Cl.
CPC .......... A63B 24/0075 (2013.01); A61B 5/112 (2013.01); A61B 5/1116 (2013.01);
(Continued)

(58) Field of Classification Search
CPC ............ A63B 24/0075; A63B 71/0622; A61B 5/1116; A61B 5/112; A61B 5/7275; G06K 9/00342; G09B 19/0038
See application file for complete search history.

(56) References Cited

U.S. PATENT DOCUMENTS 6,122,960 A  * 9/2000  Hutchings .............. A63B 24/00
                                                      73/493
7,254,516 B2 * 8/2007  Case, Jr ................ G07F 17/323
                                                      702/182
(Continued)

FOREIGN PATENT DOCUMENTS

JP       09-330424 A      12/1997
JP       2009204568 A     9/2009
(Continued)

OTHER PUBLICATIONS

International Search Report in PCT/KR2017/008506, dated Nov. 16, 2017.
(Continued)

Primary Examiner — David Phantana-angkool
(74) Attorney, Agent, or Firm — John H. Choi & Associates

(57) ABSTRACT

An automatic coaching system and method for an exercise state of a user include: a metric calculating step of calculating at least one metric by using data collected by an acceleration sensor or a location sensor worn by the user; a new coaching target metric selecting step of calculating an error rate between the calculated metric and a prestored metric reference value, selecting a new coaching target metric based on the error rate, and outputting a coaching message related to the coaching target metric; a new metric improvement verifying step of verifying new metric improvement occurrence when the new coaching target metric is not selected and outputting an alarm when the new (Continued)

metric improvement occurs; and an exercise state outputting step of outputting an alarm for an exercise state when the metric improvement and the new coaching target metric are not present.

15 Claims, 25 Drawing Sheets

Related U.S. Application Data is a continuation-in-part of application No. PCT/KR2017/008534, filed on Aug. 8, 2017, which is a continuation-in-part of application No. PCT/KR2017/008506, filed on Aug. 7, 2017.

(30) Foreign Application Priority Data

| | | |
|---|---|---|
| Mar. 10, 2017 | (KR) | 10-2017-0030394 |
| Mar. 10, 2017 | (KR) | 10-2017-0030402 |
| Jun. 22, 2017 | (KR) | 10-2017-0079255 |
| May 10, 2018 | (KR) | 10-2018-0053671 |
| Jul. 18, 2018 | (KR) | 10-2018-0083450 |

(51) Int. Cl.
*A63B 71/06* (2006.01)
*A61B 5/11* (2006.01)
*G09B 19/00* (2006.01)
*A61B 5/00* (2006.01)
*G06V 40/20* (2022.01)

(52) U.S. Cl.
CPC ........ *A61B 5/7275* (2013.01); *A63B 71/0622* (2013.01); *G06V 40/23* (2022.01); *G09B 19/0038* (2013.01); *A61B 5/1112* (2013.01); *A61B 2562/0219* (2013.01); *A63B 2024/0068* (2013.01); *A63B 2071/0625* (2013.01); *A63B 2071/0655* (2013.01); *A63B 2220/40* (2013.01); *A63B 2220/836* (2013.01); *A63B 2225/52* (2013.01)

(56) References Cited

U.S. PATENT DOCUMENTS

| | | | |
|---|---|---|---|
| 9,307,932 B2 | 4/2016 | Mariani et al. | |
| 9,616,328 B2 | 4/2017 | Song et al. | |
| 10,065,074 B1* | 9/2018 | Hoang | G09B 19/003 |
| 10,117,204 B2* | 10/2018 | Greenberg | H04L 1/08 |
| 10,307,081 B2* | 6/2019 | Nino | A61B 5/1038 |
| 10,314,520 B2* | 6/2019 | Hauenstein | G01C 21/16 |
| 11,002,547 B2* | 5/2021 | Lemarchand | G01P 13/00 |
| 11,007,406 B2* | 5/2021 | Shah | G09B 19/003 |
| 2007/0250261 A1 | 10/2007 | Soehren | |
| 2013/0110456 A1 | 5/2013 | Solinsky | |
| 2014/0118138 A1* | 5/2014 | Cobelli | A61B 5/4866 340/539.12 |
| 2015/0324636 A1* | 11/2015 | Bentley | A63F 13/00 386/227 |
| 2019/0224529 A1* | 7/2019 | Jung | A61B 5/7275 |
| 2020/0054931 A1* | 2/2020 | Martin | G06F 3/011 |
| 2021/0128979 A1* | 5/2021 | McHugh | H04Q 9/00 |

FOREIGN PATENT DOCUMENTS

| | | |
|---|---|---|
| JP | 2016041155 A | 3/2016 |
| KR | 20080102466 A | 11/2008 |
| KR | 20110067416 A | 6/2011 |
| KR | 20120059824 A | 6/2012 |

OTHER PUBLICATIONS

Written Opinion in PCT/KR2017/008506, dated Nov. 16, 2017.
International Search Report in PCT/KR2017/008533, dated Nov. 14, 2017.
Written Opinion in PCT/KR2017/008533, dated Nov. 14, 2017.
International Search Report in PCT/KR201 7/008534, dated Nov. 14, 2017.
Written Opinion in PCT/KR2017/008534, dated Nov. 14, 2017.

* cited by examiner

110

FIG. 4
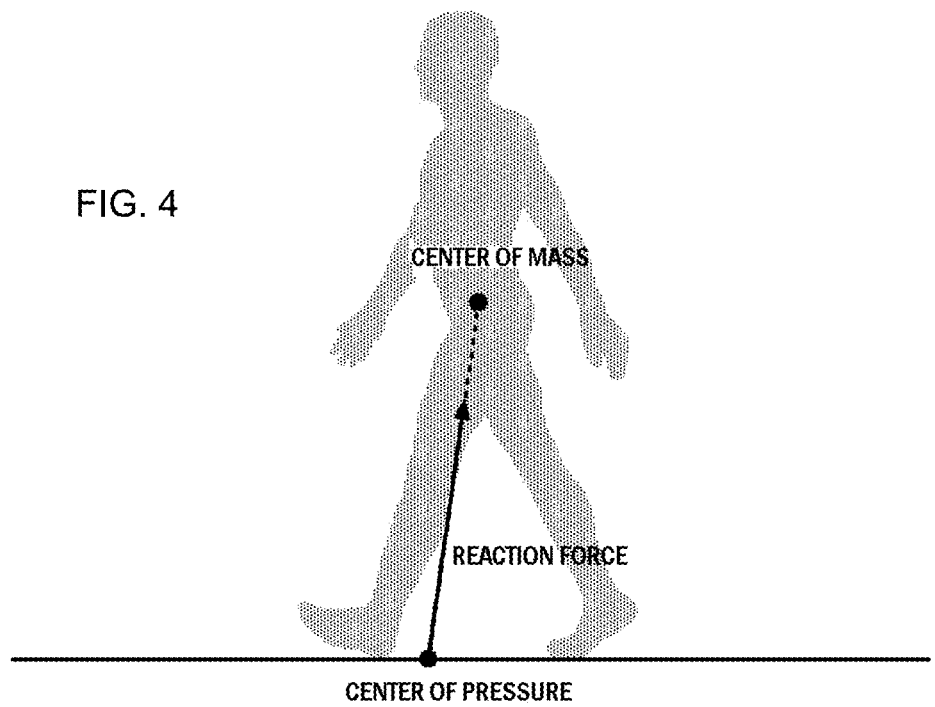
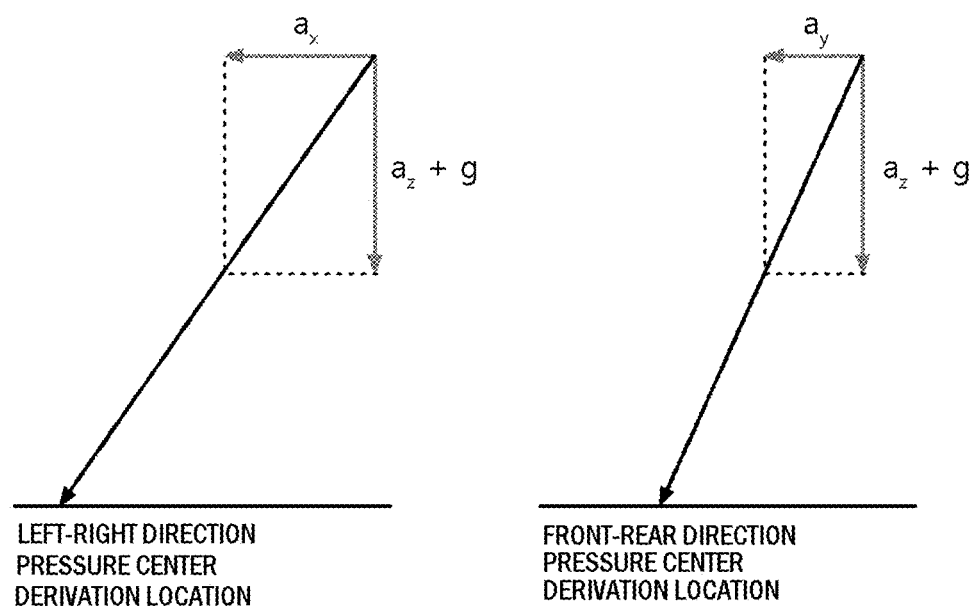
FIG. 5

AUTOMATIC COACHING SYSTEM AND METHOD FOR COACHING USER'S EXERCISE

CROSS-REFERENCE TO RELATED APPLICATION

This application claims priority to PCT/KR2017/008506, filed on Aug. 7, 2017; PCT/KR2017/008533, filed on Aug. 8, 2017; PCT/KR2017/008534, filed on Aug. 8, 2017; KR10-2018-0053671, filed May 10, 2018; and KR10-2018-0083450, filed Jul. 18, 2018; which respectively claim priority to KR10-2016-0101489, filed Aug. 9, 2016; KR10-2016-0181491, filed Aug. 9, 2016; KR10-2017-0030394, filed Mar. 10, 2017; KR10-2017-0030402, filed Mar. 10, 2017; KR10-2017-0079255, filed Jun. 22, 2017; and KR10-2017-0099566, filed Aug. 9, 2017; each of which is incorporated by reference in its entirety.

FIELD

The present invention relates to an automatic coaching system and method for coaching a user's exercise, and more particularly, to a system and a method for automatically generating and outputting a coaching value for a metric regarding exercise information, posture information, or injury risk information of a user.

BACKGROUND

It has been steadily pointed out that the amount of exercise in everyday life of modern people is significantly insufficient to maintain appropriate physical health, and accordingly, a systematic exercise method that can effectively promote health is getting more attention. As one of the exercise methods meeting the demands, there is a walking or running exercise that anyone can easily perform.

However, it has been pointed that in the case of an overweight person, an elderly person having weak joints, or the like, such a walking or running exercise causes a body weight to be applied to a knee, an ankle, or the like or gives an impact on a joint receiving ground reaction force, and as a result, there is a risk that the joint will be rather damaged due to the exercise. On the other hand, in general, in order to perform the walking or running exercise, people use a treadmill, etc. at a health center, but there are so many cases where people use an outdoor walkway, a park, etc.

However, when a floor of such an outdoor walkway, etc. is hard like asphalt, or when a person does exercise with wearing shoes that can not sufficiently absorb the impact, a person having a general health condition may also have a risk of joint damage due to the impact.

In order to prevent such problems, various research efforts have been made, such as developing a running shoe with a shock absorbing function, or developing various designs to minimize the risk of injury in the treadmill.

In the case of a group of researchers or technicians who are studying impact absorption during professional driving, the researchers or technicians have various experimental equipment for research and development. Therefore, by predicting or applying a relationship between the impact and the injury risk generated during running, a new product can be designed. However, it is almost impossible for general persons to personally estimate how much they are actually shocked by walking or running, and how much the resulting risk of injury is, other than the group that professionally conducts such research. Further, it is also practically impossible for the general persons to go to the above-mentioned specialized research facility and measure posture and injury risk of the general persons during their own running.

The prior art includes Korean Patent Registration No. 1430135 ("Footwear Sole", Aug. 7, 2014) and Korean Patent Unexamined Publication No. 2011-0107420 ("Fall Prevention and Walking Training System", Oct. 4, 2011).

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

A technical problem to be solved by the present invention is contrived to solve the problems in the related art described above and an object of the present invention is to provide a system and a method which can inform a user of an exercise posture and an injury risk degree and appropriately perform coaching by using portable equipment with which a general person may also take exercise while wearing easily.

However, it is to be understood that the technical problems to be solved by the present invention are not limited to the above problems and may be variously extended without departing from the technical spirit and scope of the present invention.

In order to solve the problem, an automatic coaching method for an exercise state of a user according to an embodiment of the present invention, as an automatic coaching method for the exercise state of the user applied in an automatic coaching system, may include: a metric calculating step of calculating at least one metric by using data collected by an acceleration sensor or a location sensor worn by the user; a new coaching target metric selecting step of calculating an error rate between the calculated metric and a prestored metric reference value, selecting a new coaching target metric based on the error rate, and outputting a coaching message related to the coaching target metric; a new metric improvement verifying step of verifying a new metric improvement occurrence when the new coaching target metric is not selected and outputting an alarm when the new metric improvement occurs; and an exercise state outputting step of outputting an alarm for an exercise state when the metric improvement and the new coaching target metric are not present.

In this case, the metric calculating step may include performing a fast Fourier transform (FFT) of data collected by the acceleration sensor and then, calculating an injury risk related metric including an instantaneous vertical loading rate (IVLR) estimation value metric based on data passing through a high-pass filter having a cut-off frequency domain of 5 Hz or more.

Further, the calculating of the injury risk related metric including an instantaneous vertical loading rate (IVLR) estimation value metric may include performing the FFT of vertical acceleration data collected by the acceleration sensor during a predetermined period and then, calculating an estimation value by a power value calculated based on the data passing through the high-pass filter.

Meanwhile, the metric calculating step may include calculating an estimation value of a pressure center path based on a mass center location of a user and calculating an exercise posture related metric including a stride length metric and a step width metric calculated based on the pressure path estimation value.

Further, in the new coaching target metric selecting step, the new coaching candidate metric may be selected based on the error rate and then, at least one metric having a highest priority among the selected new coaching candidate metrics may be selected as the new coaching target metric.

In addition, the priority may be calculated by multiplying the error rate by a weight corresponding to the new coaching candidate metric and when the new coaching target metric is selected, an alarm frequency of the new coaching candidate metric may be considered.

Further, the new coaching target metric selecting step may include storing the metric selected as the new coaching target metric in the coaching target list.

In addition, the new metric improvement verifying step may include verifying whether at least any one of the metrics stored in the coaching target list is improved at an improvement reference error rate or more.

Details of other exemplary embodiments of the present invention will be included in the detailed description of the invention and the accompanying drawings.

According to the present invention, there is a big effect that by using equipment that can be easily carried and which can be easily worn on the body such as the head, waist, etc., a general person can receive coaching for an exercise posture by himself/herself or can very easily measure the risk of injury during running. In particular, as in modern times in a situation where the majority of general persons require self-diagnosis while exercising for health, the general persons can measure such a risk of injury by themselves without using a professional management institution. Therefore, there is an effect of remarkable convenience and economic enhancement in health promotion of the general persons.

Further, in terms of a device configuration, according to the present invention, there is a great advantage that only a sensor measuring a dynamic physical quantity of a user can be used such as an acceleration sensor. That is, in the related art, there are various problems including device durability and life-span degradation problems, problems of production and use of separate devices according to user's body dimensions, and the like by using a pressure sensor which is pressed by a user's foot to recognize walking. However, in the case of the present invention, since a technique of disposing the pressure sensor, which is a cause of such a problem, in a foot portion is completely excluded, various problems as described above are fundamentally eliminated. Of course, it is natural that such effects as the enhancement of user convenience and the economic enhancement of each user or producer can also be obtained through the elimination of the problems.

Further, from the viewpoint of user experience (UX), when an alarm is given too frequently for coaching, the user may feel uncomfortable and the alarm may greatly affect efficient exercise. Therefore, an automatic coaching system of the present invention can preferentially correct an exercise posture which is most important and is to be urgently improved.

However, the effects of the present invention are not limited to the above effects and may be variously extended without departing from the technical spirit and scope of the present invention.

BRIEF DESCRIPTION OF DRAWINGS

The foregoing summary, as well as the following detailed description of presently preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIGS. 3, 4, 5, 6, 7A-7B, and 8 are diagrams for describing an embodiment of a method for calculating a metric related to an exercise posture of the present invention.

Figure 1:
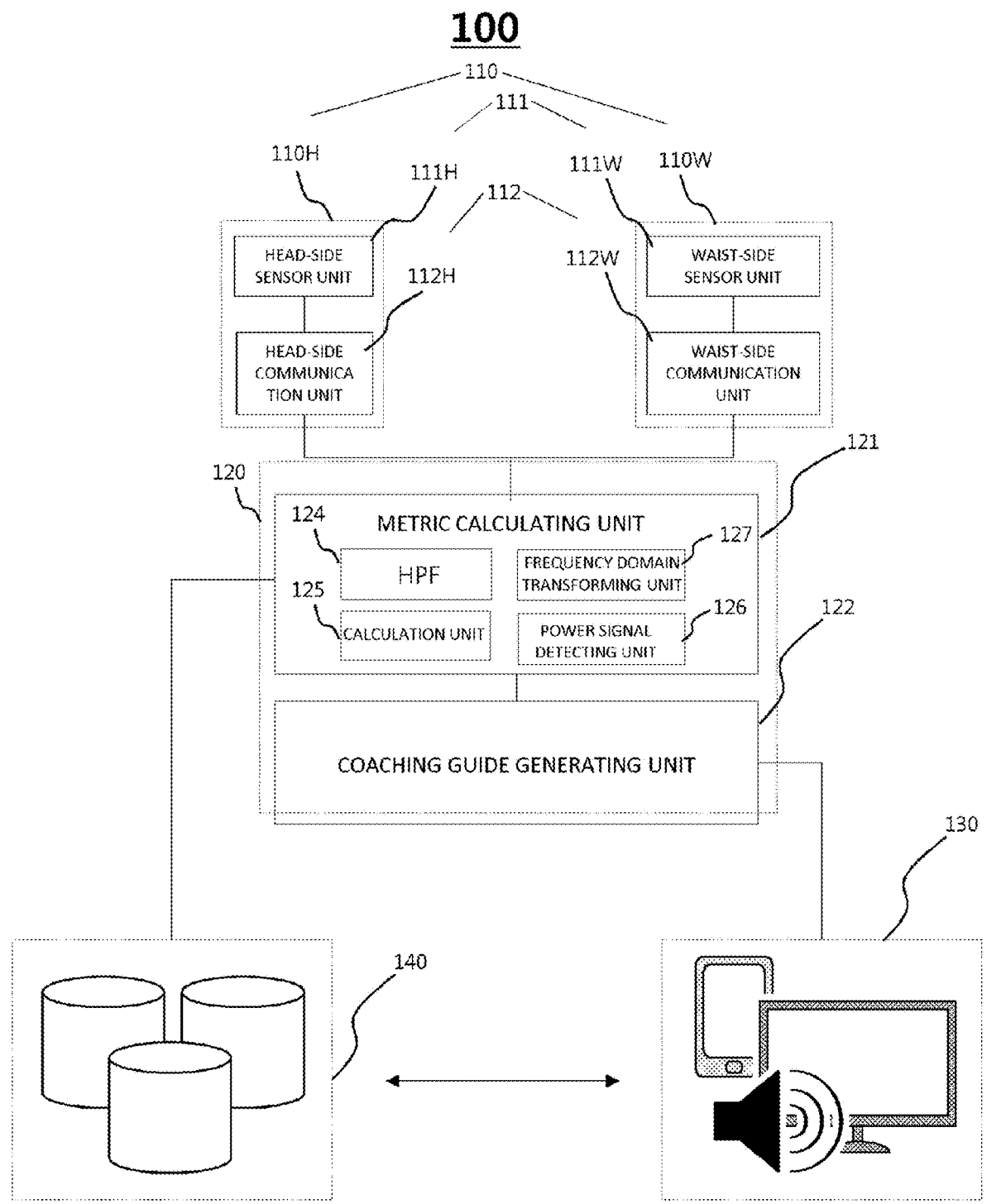
FIG. 1 is a block diagram illustrating an embodiment of an automatic coaching system of the present invention.

To facilitate an understanding of the invention, identical reference numerals have been used, when appropriate, to designate the same or similar elements that are common to the figures. Further, unless stated otherwise, the features shown in the figures are not drawn to scale, but are shown for illustrative purposes only.

DETAILED DESCRIPTION

Certain terminology is used in the following description for convenience only and is not limiting. The article "a" is intended to include one or more items, and where only one item is intended the term "one" or similar language is used. Additionally, to assist in the description of the present invention, words such as top, bottom, side, upper, lower, front, rear, inner, outer, right and left may be used to describe the accompanying figures. The terminology includes the words above specifically mentioned, derivatives thereof, and words of similar import.

EXPLANATION OF REFERENCE NUMERALS AND SYMBOLS

100: Automatic coaching system
110: Sensor signal collecting unit
120: Control unit
121: Metric calculating unit
122: Coaching guide generating unit
130: Coaching guide output unit Advantages and features of the present disclosure, and methods for accomplishing the same will be more clearly understood from exemplary embodiments described in detail below with reference to the accompanying drawings. However, the present invention is not limited to the embodiments set forth below, and will be embodied in various different forms. The present embodiments are just for rendering the disclosure of the present invention complete and are set forth to provide a complete understanding of the scope of the invention to a person with ordinary skill in the technical field to which the present invention pertains, and the present invention will only be defined by the scope of the claims.

It is also to be understood that the terminology used herein is for the purpose of describing embodiments only and is not intended to limit the present invention. In this specification, singular forms include even plural forms unless the context clearly indicates otherwise. It is to be understood that the terms 'comprise' and/or 'comprising' used in the specification are intended to be inclusive in a manner that does not exclude the presence of stated components, steps, operations, and/or elements does not exclude the addition.

Unless otherwise defined, all terms (including technical and scientific terms) used in the present specification may be used as the meaning which may be commonly understood by the person with ordinary skill in the art, to which the present disclosure pertains. Further, terms defined in commonly used dictionaries should not be interpreted in an idealized or excessive sense unless expressly and specifically defined.

Hereinafter, preferred embodiments of the present invention will be described in detail with reference to the accompanying drawings. The same reference numerals are used for the same constituent elements in the drawings and redundant explanations for the same constituent elements are omitted.

Automatic Coaching System

FIG. 1 is a block diagram illustrating an embodiment of an automatic coaching system of the present invention.

The automatic coaching system 100 of the present invention may include a sensor signal collecting unit 110, a control unit 120, and a coaching guide output unit 130.

The sensor signal collecting unit 110 may measure a user's dynamic physical quantity such as an acceleration, a speed, and a position, and may include a sensor unit 111 and a communication unit 112. In this case, hardware of the sensor unit 111 basically includes an acceleration sensor in three axial directions including basically up and down, right and left, and front and rear. In this case, the sensor unit 111 may further include a sensor capable of measuring the acceleration in six axial directions by incorporating a gyroscope in the acceleration sensor. Alternatively, the sensor signal collecting unit 110 may be, for example, a sensor that measures 9-axis posture including an acceleration sensor, a gyro sensor, and a geomagnetic sensor. Alternatively, the sensor signal collecting unit 110 includes a position sensor of a GPS signal, etc., to measure even a user position, for example, and may include an appropriate sensor adopting an ultra-accurate satellite navigation technique or an indoor positioning technique having higher accuracy than a GPS in recent years. Further, those skilled in the art may include an appropriate sensor considering appropriate sensing and power use as the sensor signal collecting unit 110.

The communication unit 112 may transmit an original signal collected by the sensor unit 111 to the control unit 120 or may be serial communication such as SPI, I2C, UART, etc., according to a physical location of the control unit 120 of the sensor unit or wireless communication such as WiFi, Bluetooth, NFC, etc. That is, the communication unit 112 may be implemented by wire communication through wiring, or wireless communication such as Bluetooth, WiFi, NFC, etc., that is, may select and adopt an appropriate form according to a required condition or required performance.

Figure 2A:
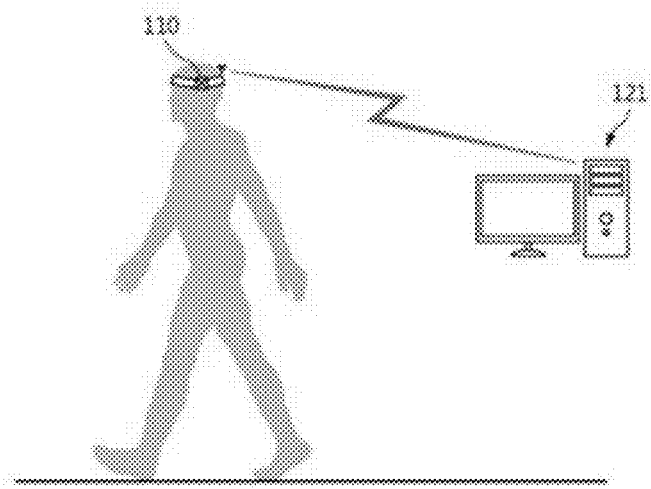
FIGS. 2A-2E are diagrams schematically illustrating a wearing location of a sensor signal collecting unit of the present invention.
Figure 2B:
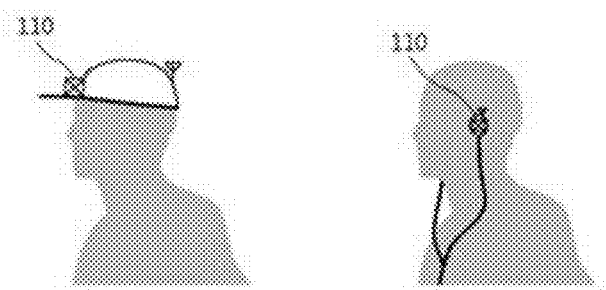
Figure 2C:
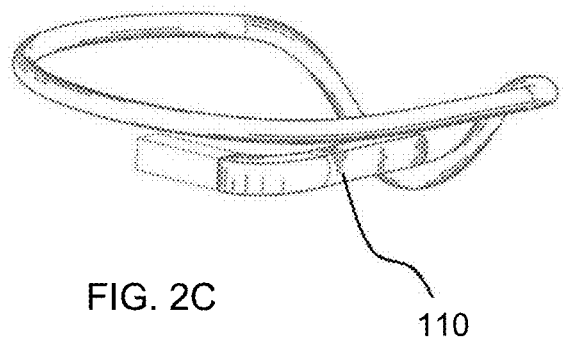
Figure 2D:
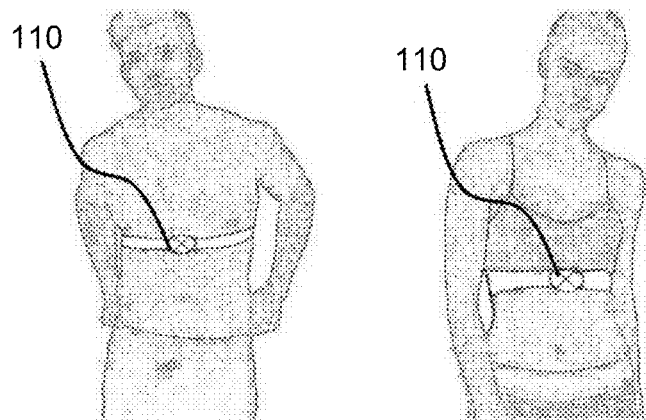

Meanwhile, the sensor signal collecting unit 110 may be worn on various parts of the user's body such as the head, the waist, the chest, etc. as illustrated in FIGS. 2A to 2E at a wearing position. When the sensor signal collecting unit 110 is worn on the head, the sensor signal collecting unit 110 may be included in a hair or head band as illustrated in FIG. 2A, may be included in a hat or an earphone as illustrated in FIG. 2B, or may be included in wearable glasses as illustrated in FIG. 2C, for example. Alternatively, when the sensor signal collecting unit 110 is worn on the chest, the sensor signal collecting unit 110 may be included in a chest band as illustrated in FIG. 2D. Alternatively, for example, as a specific example of a wearing state, a head-side sensor 111H to be worn on a head side may be configured in a form put in the ear such as the earphone and a waist-side sensor 111W to be worn on a waist side may be configured in a form put in a belt.

Of course, the present invention is not limited thereto and for example, it is natural that the head-side sensor 111H may be variously modified and implemented as a hair or head band form, a glasses form, a form put and attached into a separate hat, a helmet form, etc. Further, although not illustrated in the drawing, the sensor signal collecting unit 110 may be worn anywhere on an upper body excluding the user's arm and for example, when the sensor signal collecting unit 110 is worn on a chest portion, the sensor signal collecting unit 110 may be variously modified and implemented in a form to be accommodated in or put and attached into a chest pocket of a garment, a form to be worn using a separate vest or harness, and the like.

Figure 2E:
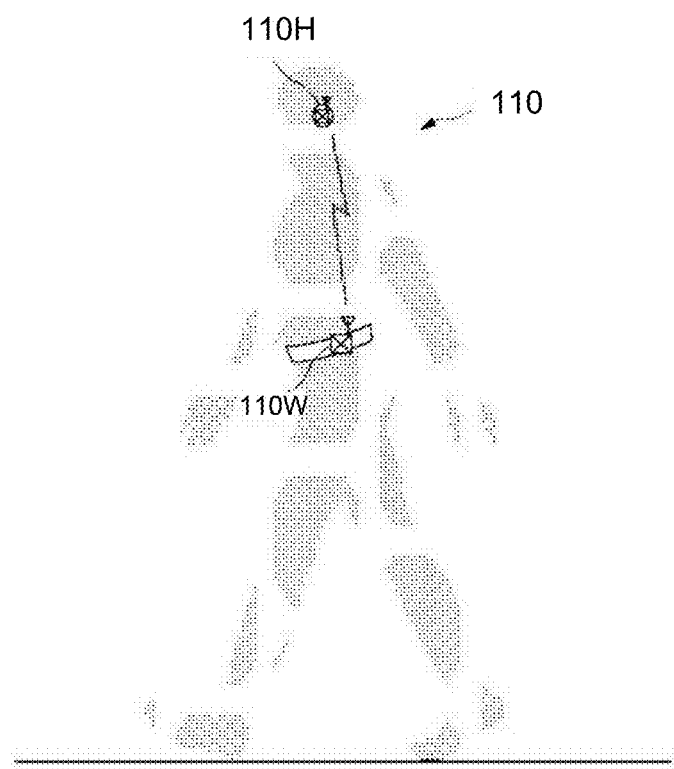

In this case, only one sensor signal collecting unit 110 may be worn as illustrated in FIG. 2A or a plurality of sensor signal collecting units 110 may be worn as illustrated in FIG. 2E. For example, the sensor signal collecting unit 110 may be worn on the head and/or waist. FIG. 1 is a block diagram for a case where the sensor unit 111 is simultaneously installed on the head side 111H and the waist side 111W. However, in regard to the sensor unit 111, only any one of the head side 111H and the waist side 111W may be installed.

The head-side sensor 111H may include an acceleration sensor and a position sensor in head-side 3-axis directions including up and down, left and right, and front and rear. Further, the waist-side sensor 111W may include an acceleration sensor in waist-side 3-axis directions including up and down, left and right, and front and rear. The position sensor may be located on the waist side 111W.

The head-side or waist-side 3-axis direction acceleration sensor may further include an angular velocity sensor such as a gyroscope, etc. and in general, may select and use an appropriate sensor used for measuring an acceleration in a 3-axis direction. The position sensor may adopt, for example, a GPS sensor, etc. and in recent years, an ultra-accuracy satellite navigation technique having higher accuracy than a GPS has been developed. Therefore, a sensor to which such a technique is applied may be used.

In the present invention, when measuring the user's dynamic physical quantity for posture derivation, a value measured at a position shown most similar to the exercise of the center of mass of the user's body may be used. For example, the acceleration in the left-right direction may be measured on the head side, the acceleration and the position in the front-rear direction may be measured on the waist side, and the acceleration in the up-down direction may be measured on the head side and/or the waist side.

More specifically for the acceleration in the up-down direction, the acceleration in the up-down direction is fairly accurate when measured from either the head or waist side, so that the measured value at either the head or waist side is selectively used or an average value of the values measured on both sides may be used, or the like, and therefore, the acceleration in the up-down direction may be appropriately selected.

Of course, since the acceleration sensor may generally measure the acceleration in all of the 3-axis directions including the up-down direction, the left-right direction, and the front-rear direction, it is possible to perform various calculations to be described below by using up-down, left-right, and front-rear-direction acceleration collected by the head-side sensor 111H alone or the waist-side sensor 111W alone. However, when walking or running, a left-right motion at the head and the left-right motion at the center of mass of the user's body are more similar to each other and further, a front-rear motion at the waist and the front-rear motion at the center of mass of the user's body are relatively more similar to each other. Moreover, the up-down motions are similar to each other at all of the head, the waist, and the center of mass. Meanwhile, in an exercise recognition method of the present invention to be described below, ultimately, exercise recognition or posture derivation is performed using the dynamic physical quantity at the center of mass of the user's body. Taking all the situations into consideration, by measuring the left-right-direction acceleration on the head side, measuring the front-rear direction acceleration on the waist side, measuring the up-down direction acceleration by appropriately selecting either the head side or the waist side as desired or calculating the up-down direction acceleration with an average value through measurement at both sides, it is possible to obtain an effect that final exercise recognition or posture derivation is greatly accurately performed.

As devices for measuring the exercise quantity in the related art, a pressure sensor provided in a shoe or a footrest directly pressed against the foot for monitoring the user's walking is used. As a result, the damage of the sensor occurs quickly and the durability and life-span of the device are shortened. In addition, there are problems including degradation of walking recognition and analysis accuracy due to device damage during use, degradation of convenience and economical efficiency due to frequent device replacement, and the like. Further, when such a device is provided in the shoe, a separate device is required for each user according to the size of the user's foot, and as a result, there are problems including an increase in degradation of the convenience and economical efficiency of the user, occurrence of an economic burden due to separate production for each size for a producer, and the like.

However, according to the present invention, in performing walking recognition, by breaking from a concept of using pressure applied by the foot totally, and the user's dynamic physical quantity, such as the acceleration, the speed, and the position measured at the head or waist of the user is measured, and recognition, detection, and analysis of the walking may be implemented by applying an analysis algorithm which is characteristic in the present invention to be described below.

As described above, the present invention differs from the related art in terms of measurement position and measurement physical quantity. At this time, a root cause of the various problems pointed out in the related art comes from a technical configuration of 'placing the pressure sensor at the foot part', and according to the embodiment, the various problems may be fundamentally removed only by such a configuration.

Meanwhile, the control unit 120 may include a metric calculating unit 121 and a coaching guide generating unit 122. In this case, the metric calculating unit 121 and the coaching guide generating unit 122 may be physically distributed and arranged. For example, the metric calculating unit 121 may be formed on one substrate in the form of an integrated circuit with the sensor signal collecting unit 110 so as to perform various operations or in the form of a separate computer or the like. Alternatively, the control unit 120 may be implemented in a smart phone used in the related art in an app form, and the like and as such, various modifications may be achieved.

The coaching guide generating unit 122 may be located in a coaching guide output unit 130 in a software module form. Alternatively, the sensor signal collecting unit 110, the metric calculating unit, and the coaching guide generating unit 122 may be physically located as one hardware and software module. Those skilled in the art may appropriately distribute and locate the metric calculating unit 121 and the coaching guide generating unit 122 by considering hardware constraints such as performances of a battery and a processor, etc.

The coaching guide output unit 130 may convert guide information including an alert signal generated by the coaching guide generating unit 122 and/or a stride length correction amount into information which may be recognized by the user, which includes at least one of sound, illustration, or video and output the converted information.

For example, when the coaching guide output unit 130 is an earphone and the stride length correction amount is calculated and the stride length needs to be thus reduced, a voice coaching such as "Reduce your stride length." or an alarm sound is output to induce the user to recognize that the stride length is not an optimal stride length and change a walking posture. Alternatively, the coaching guide output unit 130 may output coaching guide information with an illustration or video in the form of a smart phone, a computer, a dedicated display, a wearable display (e.g., Google Glass), or the like.

Further, the coaching guide generating unit 122 or the coaching guide output unit 130 may be configured to transmit the walking attitude derived by the metric calculating unit 121 to the external database 140 and cumulatively store the derived walking posture. A user who needs such a walking or running exercise analysis may be a general person who performs daily walking or jogging to promote health or an expert who is trained to enhance a physical ability and the exercise analysis data is naturally preferable to be accumulated to see a temporal change. In addition, when a large amount of exercise analysis data is accumulated and stored, such data is utilized as big data to be used in various statistics or analyses, etc., that is, the exercise analysis data may be variously utilized.

Meanwhile, the coaching guide output unit 130 may generate and reproduce a guide message with respect to a coaching target metric having a highest priority and provide coaching to the user. The coaching guide output unit 130 may output the guide message to the user using an auditory method or a visual method. For example, in the case of voice coaching, the coaching guide output unit 130 may generate the coaching target metric having the highest priority as a natural language based message and notify the user of the coaching target metric. This may be applied to various sound reproducing devices including earphones, headphones, speakers, and the like and may provide a value and an evaluation for the corresponding coaching metric and provide a correction method.

Further, coaching using visual display may be applied to devices using various visual displays including a mobile phone screen, a smart watch, a monitor screen, an AR display, an LCD display, and the like and provide the value and the evaluation for the corresponding coaching target metric and provide the correction method through a text, a moving picture, etc.

As a specific utilization example, the coaching guide output unit 130 may provide to the user coaching such as "Be careful of M1, M2, and M3" and "Instantaneous vertical load rate is too large as 150 N/s. Please, run more lightly." through the sound reproducing device in the case of voice coaching. Alternatively, the coaching guide output unit 130 may output coaching such as "Upward/downward movement is too large. Raise the number of steps and jump at leap.", "Your stride length is too large. Raise the number of steps." through a visual display device by using the text, emoticons, or a short moving picture and provide the coaching to the user in the case of visual display coaching.

The above-described automatic coaching method according to the present invention may be set such that an entire cycle is periodically repeated every n seconds of an operation cycle. Such an automatic coaching method may be applied to the automatic coaching system described above.

Figure 25:
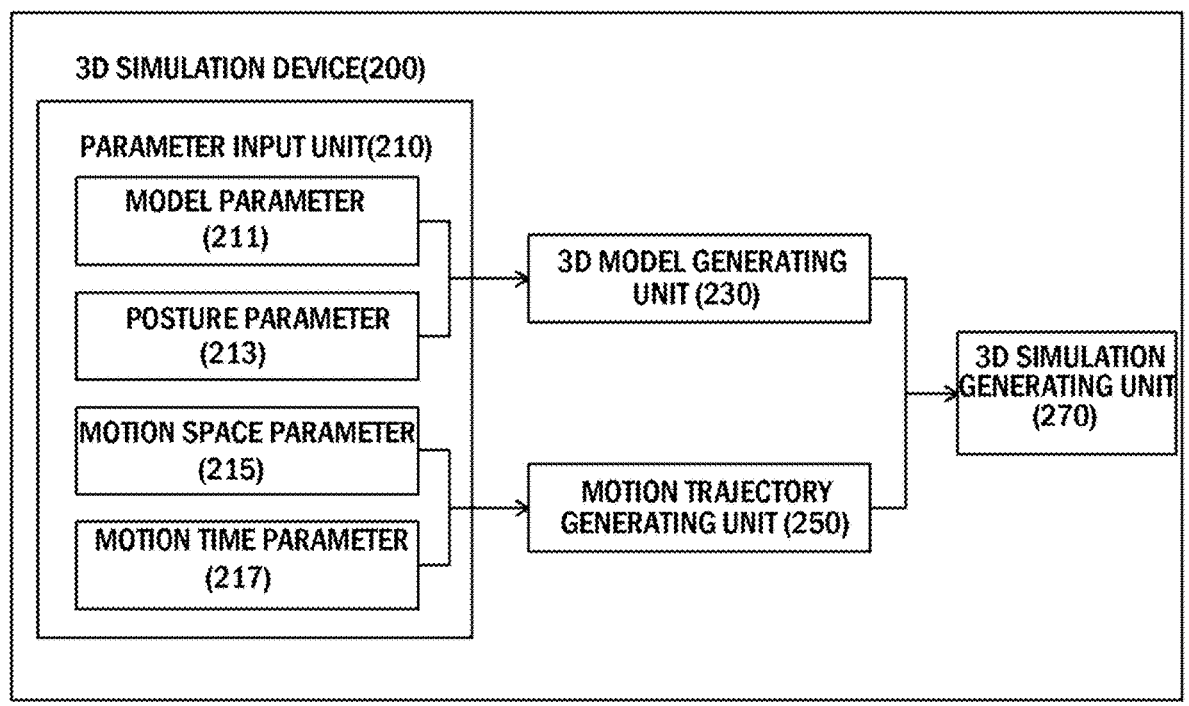
FIG. 25 is a block diagram illustrating a 3D simulation device according to an embodiment of the present invention.
Figure 26:
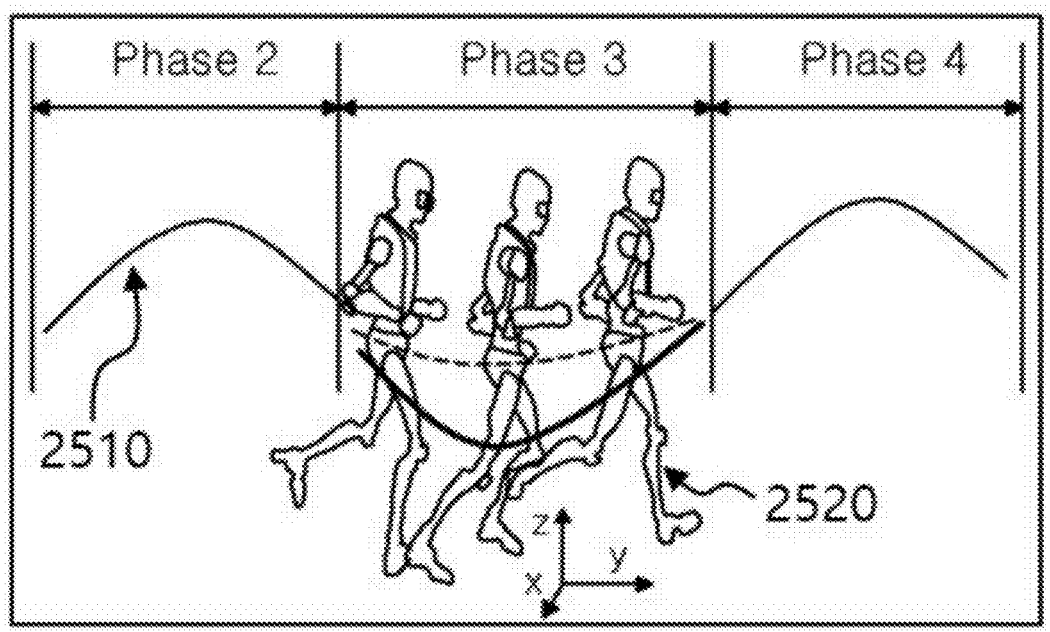
FIG. 26 is a diagram illustrating a screen generated by a 3D simulation device according to an embodiment of the present invention.

In this case, the coaching guide output unit 130 may be a 3D simulator illustrated in FIGS. 25 and 26.

Referring to FIG. 25, a 3D simulation device 200 includes a parameter input unit 210, a 3D model generating unit 230, a motion trajectory generating unit 250, and a 3D simulation generating unit 270.

The parameter input unit 210 receives a model parameter 211, a posture parameter 213, a motion space parameter 215, and a motion time parameter 217 based on an external input. The external input is an input from the user or as the external input, and the exercise of the user is recognized from an exercise recognition device and input.

The model parameter 211 as a parameter relating to an external shape of the user includes at least one of a height, a weight, a foot length, a leg length, an age, a gender, and wearing information. The wearing information includes a type, a name, and a brand of a product worn by the user. The products worn by the user includes accessories such as watches, clothes, shoes, and the like.

The posture parameter 213 as a parameter relating to the posture of the user includes at least one of a step width, a step angle, and a head vertical angle. The step width refers to a mean value of a distance between the legs and the step angle refers to a mean value of a leg angle. The head vertical angle refers to a mean value of a vertical angle of the head.

The motion space parameter 215 as a parameter related to a spatial trajectory of a user's motion includes, when the user performs running exercise, at least one of a vertical oscillation during stance, a vertical oscillation during flight, instantaneous vertical loading rate (IVLR), average vertical loading rate (AVLR), impact force, impulse, left/right stability, left/right balance, a stride length, a foot strike pattern, pelvic vertical rotation, pelvic lateral rotation, and a head lateral angle. The motion space parameter 215 includes, when the user performs walking exercise, at least one of the vertical oscillation during single stance, the vertical oscillation during double stance, the left/right stability, the left/right balance, the stride length, the foot strike pattern, the pelvic vertical rotation, the pelvic lateral rotation, and the head lateral angle.

The motion time parameter 217 as a parameter related to a time trajectory of the user's motion includes, when the user performs the running exercise, at least one of a single stance time, a single flight time, and a cadence. The motion time parameter 217 includes, when the user performs the walking exercise, at least one of the single stance time, a double stance time, and the cadence.

The 3D model generating unit 230 generates a 3D model of the user based on the model parameter 211 and the posture parameter 213.

The motion trajectory generating unit 250 generates a motion trajectory of the user based on the motion space parameter 215 and the motion time parameter 217. A detailed operation of the motion trajectory generating unit 250 will be described below in detail with reference to FIGS. 5 to 9B.

The 3D simulation generating unit 270 applies the motion trajectory to the 3D model to generate a 3D simulation of the user.

A screen generated by the motion trajectory generating unit 250 and the 3D simulation generating unit may include, for example, a trajectory 2510 and a 3D simulation screen 2520 which is an avatar of the user as illustrated in FIG. 26.

Figure 23:
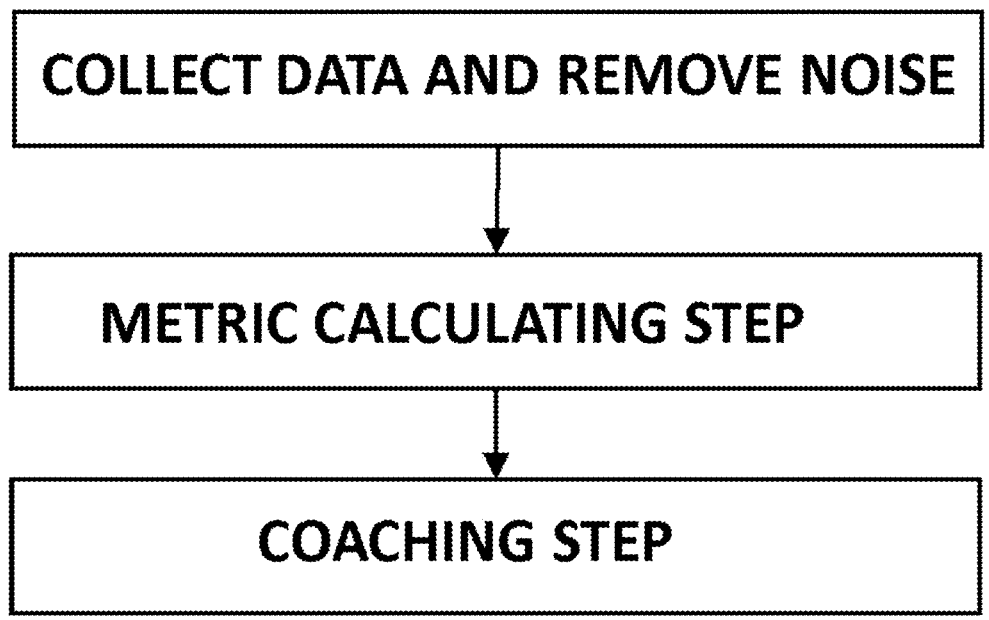
FIG. 23 illustrates an exercise recognition operation according to an embodiment of the present invention.

Meanwhile, an overall operation of the automatic coaching method is illustrated in FIG. 23.

First, sensor data is collected and noise is removed through the sensor signal collecting unit 110 mentioned above. Thereafter, the metrics are calculated and the coaching is performed.

Figure 24:
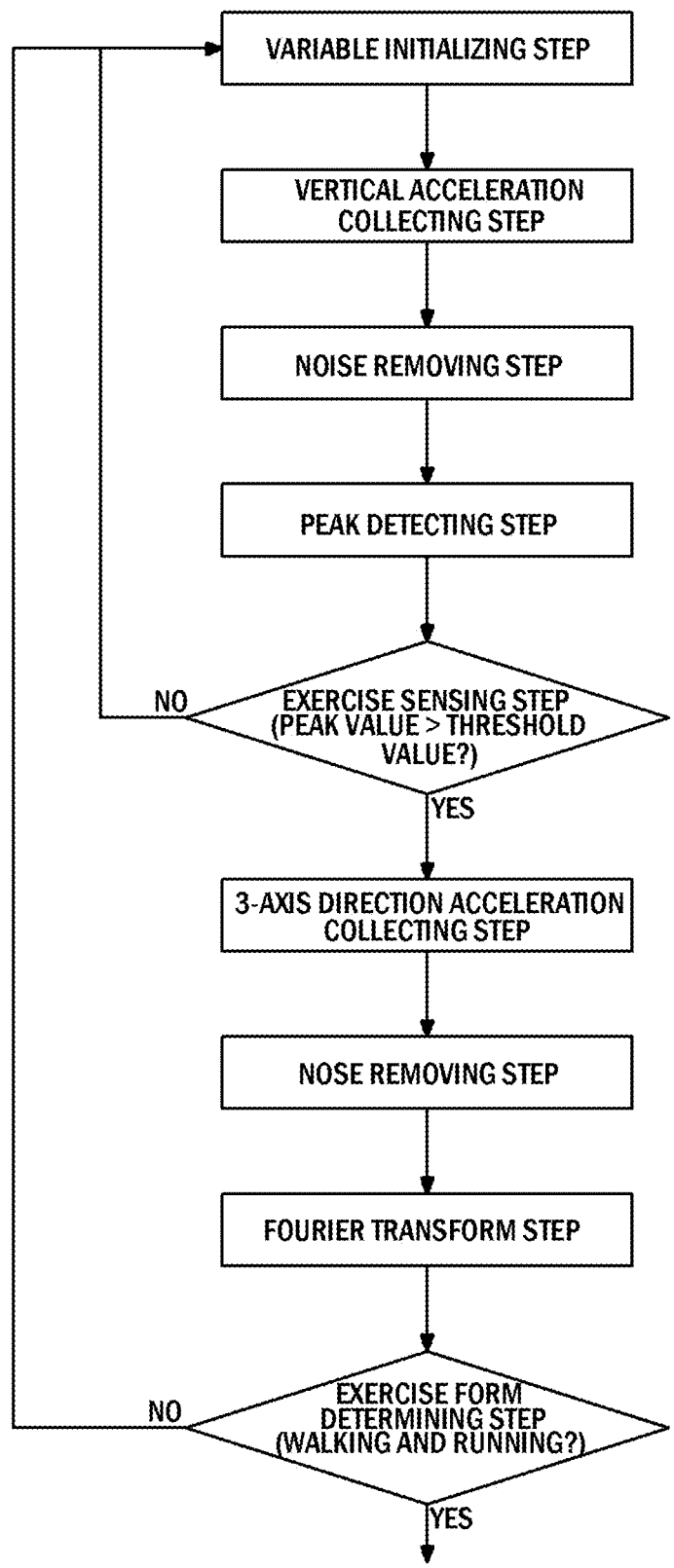
FIG. 24 is a flowchart illustrating a step of collecting data and removing noise according to an embodiment of the present invention.

A collection operation of the sensor data is performed by the control unit 120 and, for example, performed as illustrated in FIG. 24.

As illustrated in FIG. 24, the data collection and noise removal step includes a vertical acceleration collection step, a peak detection step, a motion detection step, a 3-axis direction acceleration collection step, a Fourier transform step, and an exercise form determining step. In the data collection and noise removal step, whether the exercise occurs in the user and whether the exercise corresponds to walking or running if the exercise occurs are recognized.

As illustrated in FIG. 24, initially, data variables to be collected are initialized and a ready-to-perform-exercise recognition is thus made.

In the vertical acceleration collection step, all of 3-axis direction accelerations $a_x$, $a_y$, and $a_z$ are not collected, but a vertical acceleration $a_z$ is collected first. Although the collected vertical acceleration $a_z$ may be used as it is, it is more preferable to pass through a predetermined band-pass filter to carry out a noise removal step of removing noise. In this case, the band-pass filter may be formed at 0.1 to 5 Hz corresponding to a walking or running frequency of a general person, for example.

In the peak detection step, a peak of the vertical acceleration $a_z$ collected as such is detected and in the exercise detection step, it is determined whether a peak value of the vertical acceleration $a_z$ is equal to or more than a predetermined threshold value to determine whether the exercise occurs. In the exercise detection step, when it is determined that the exercise does not occur, a variable is initialized by returning to an initial ready step again.

In addition, when performing the analysis in the control unit 120, when the 3-axis direction accelerations $a_x$, $a_y$, and $a_z$ are continuously collected, unnecessary calculation loads are generated when there is no exercise, and as a result, problems including power consumption, heat dissipation, and the like may occur. On the other hand, in the case where the user moves as much as the user sits down or turns his or her body, or when the user moves about to walk or run, a greatest difference is a degree to which the user shakes up and down, that is, the vertical acceleration $a_z$. Accordingly, the control unit 120 first collects the vertical acceleration $a_z$ of the user wearing the sensor, determines that the user is walking or running when the value reaches a certain threshold value or more, and starts real exercise detection from that time, thereby preventing the unnecessary calculation load problem described above.

In the 3-axis direction acceleration collection step, when the peak value of the vertical acceleration $a_z$ is equal to or more than the predetermined threshold value as described above, the 3-axis direction accelerations $a_x$, $a_y$, and $a_z$ are collected. Similarly even in this case, although the collected 3-axis direction accelerations $a_x$, $a_y$, and $a_z$ may be used as they are, it is more preferable to perform the noise removal step of removing the noise by passing through the predetermined band-pass filter. The band-pass filter in this case may be formed similar to the band-pass filter used for removing the noise of the vertical acceleration $a_z$ described above or may be appropriately changed and set.

In the Fourier transform step, the 3-axis direction accelerations $a_x$, $a_y$, and $a_z$ are Fourier-transformed to derive a frequency response graph and in the exercise form determining step, the frequency response graph is compared with a predetermined frequency response open or size criterion to determine whether the exercise form is walking and running exercise or other exercise. When it is determined that the exercise corresponding to the walking and running exercise does not occur in the exercise form determining step, the variable is initialized by returning to an initial ready step again and otherwise, when it is determined that the walking and running exercise occurs, an acceleration based exercise state deriving step is performed.

As described above, in the exercise form determining step, it is determined whether the exercise of the user is in walking and running states.

Meanwhile, hereinafter, a detailed configuration of the control unit 120 will be described.

Configuration Of Metric Calculating Unit

The metric calculating unit 121 of the control unit 120 receives a signal from the sensor signal collecting unit 110 to derive various metrics related to walking or running exercise information, posture information, and an injury risk by using a 3-axis direction acceleration and/or a location signal. The generated metrics are described below, for example.

In this case, various metrics are basically generated by using a sensing value of each direction acceleration, etc., collected by the sensor signal collecting unit 110 or other metrics and for easy description, in this specification, values calculated by using other metrics are expressed as the lower metric and metrics using a basic sensing value are expressed even as the higher metric. Some of the metrics may be derived by using a GPS location sensor of the coaching guide output unit, etc., for example.

The metric values provided to the user include exercise information, posture information, and injury risk information. The exercise information metric values include time (sec.), distance (km), pace (m/sec.), virtual pace (m/sec.), calories (kcal), altitude (m), and step number (steps). The posture information metric values include forward distance traveled during stance phase (m), forward distance travelled during flight phase (m), step width (cm), step angle (deg.), head angle (deg.), vertical oscillation (m), left (L) vertical oscillation (m), right (R) vertical oscillation (m), vertical oscillation during stance phase (m), vertical oscillation during flight phase (m), ground contact time (sec.), left ground contact time (sec.), right ground contact time (sec.), flight time (sec.), left flight time (sec.), right flight time (sec.), contact-flight ration Tf/Tc (%), ground reaction force GRF (Newtons), and center of pressure COP (Newtons). The injury risk information metric values include a max force (Newtons), a left max force (Newtons), a right max force (Newtons), an inpact force (Newtons), an impulse (Newton-sec.), a symmetry (%), a stability (%), a left stability (%), a right stability (%), a leg stiffness (Newton/m) which is the body weight (BW)=mass*g over meters, an average vertical loading rate (Newton/sec.) which is BW over sec., and an instantaneous vertical loading rate (Newton/sec.) which is BW over sec. The metric values of forward distance traveled during stance phase, forward distance travelled during flight phase, left vertical oscillation, right vertical oscillation, vertical oscillation during stance phase, vertical oscillation during flight phase, left ground contact time, right ground contact time, left flight time, right flight time, left max force, and right max force are each a lower metric derived from a higher metric.

Calculation Implementation Example of Exercise Posture Related Metric

The metric calculating unit 121 of the present invention senses the user's exercise and calculates various metrics related to distinction of the walking/running or determination of the posture. Hereinafter, a metric calculation example of the present invention will be described in detail with reference to FIGS. 3 to 8.

Figure 3:
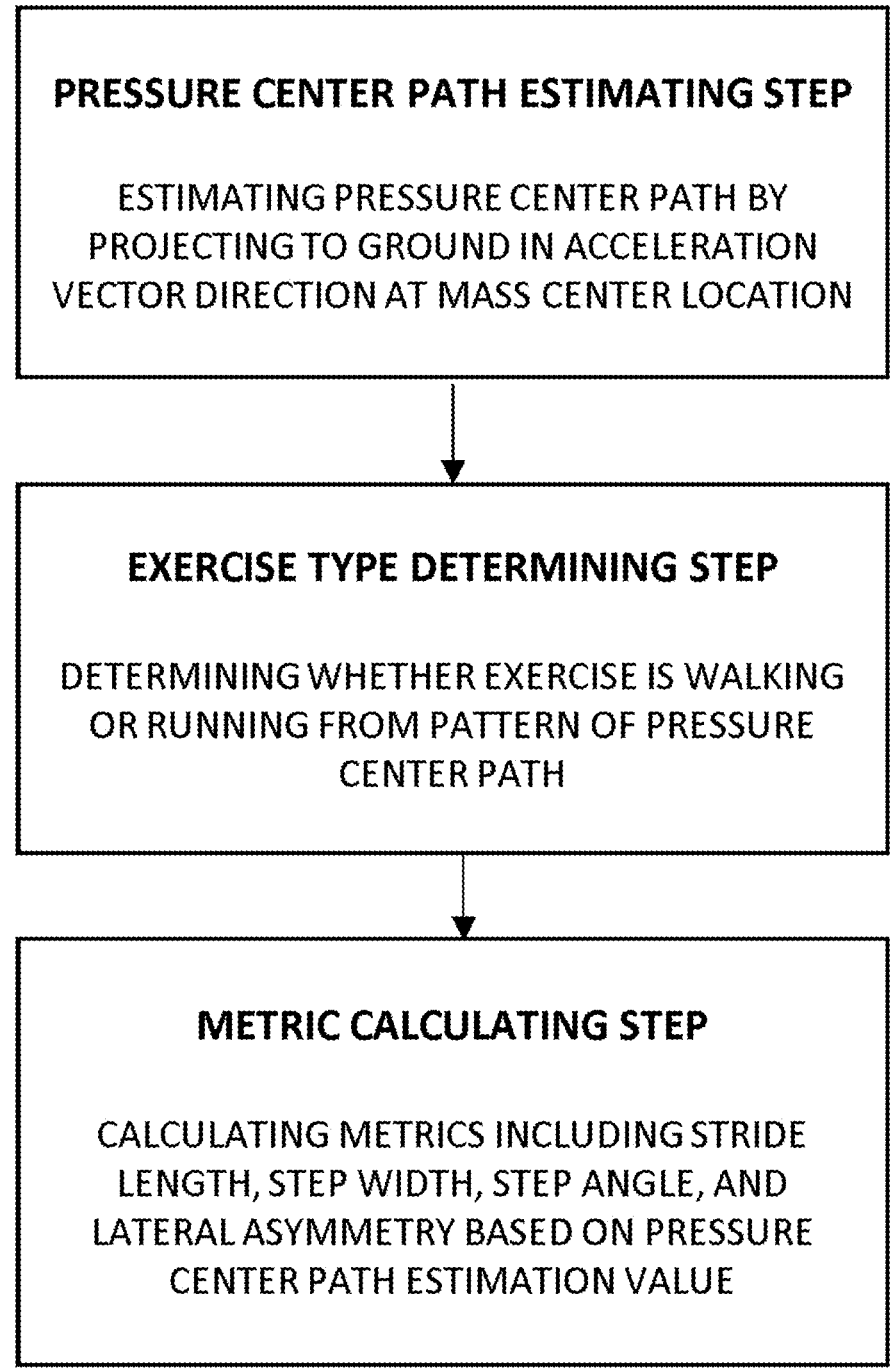

For example, the stride length, the step width, the step angle, and lateral asymmetry, which are metrics for deriving the exercise posture, may include a pressure center path estimation step, an exercise type determining step, and an exercise posture related metric calculating step as illustrated in FIG. 3.

For example, in the pressure center path estimation step, by using exercise state values of a user mass center calculated by using the 3-axis direction accelerations $a_x$, $a_y$, and $a_z$ sensed by the sensor unit 111, a pressure center path is estimated by projecting to the ground in an acceleration vector direction at a mass center location.

The metric calculating unit 121 acquires the speed and the location by integrating the 3-axis direction accelerations collected by a 3-axis direction acceleration sensor 111 of the sensor unit 111 or using location information of a location measurement sensor of the sensor unit 111. In this case, it is preferable to convert the speed and the location into a data value at the user mass center and analyze the data value based on basic data (height information) received from the user in the related art and sensor data collected by the sensor unit 111. In this case, an exercise data value at the user mass center may be calculated by a method for appropriately multiplying a previously acquired gain value by using body information such as user's height information, etc.

More specifically, in a mass center acceleration deriving step, a value of each of the 3-axis direction accelerations $a_x$, $a_y$, and $a_z$ is multiplied by a predetermined gain value to derive the acceleration of the user mass center. In general, when exercise of any object is analyzed, the exercise is analyzed based on exercise of a mass center of the object and since variable values used in the above analysis are measured in the head of the user, the variable values are converted into the exercise state values of the mass center. The gain value may be represented by a constant vector y and previously acquired by using body information such as user's height information, etc.

In the mass center speed and location deriving step, the speed and the location of the user mass center are derived by using previously measured user's height information, user location information, and mass center acceleration. That is, the speed and the location of the mass center (obtained by adding an integral constant value) may be acquired by integrating the mass center acceleration acquired as described above or the speed and the location of the mass center may be acquired by using the user location information temporally measured by the location measurement sensor. There is an error between the two calculated values as much as the integral constant value and speed and location values of the accurate mass center may be obtained by appropriately comparing the calculation values.

As described above, according to the present invention, it is possible to accurately determine whether the user is walking or running using the acceleration, the location, and the like measured at the user's head and further, it is possible to accurately determine how the mass center of the user performs the exercise in walking or running (that is, how the acceleration, the speed, and the location of the mass center are shown). Therefore, based thereon, various elements of walking or running postures may be derived and used for the correction of the posture.

Meanwhile, the pressure center path may be estimated from the exercise state value (acceleration/speed/location per time for each of directions, frequency analysis, etc.) at the mass center of the user.

The human body behaves by using reaction pressure applied to a supporting foot during the walking or running. The sum of the reaction pressures is called ground reaction force (GRF) and the center of the pressure is called a center of pressure (COP). It is revealed that the ground reaction force generated in this case has characteristics of being directed to the center of mass (COM) of the human body from the pressure center. FIG. 4 schematically illustrates a relationship between the center of mass and the center of pressure. In the embodiment, the center of pressure is inferred by projecting to the ground in the vector direction of force measured at the center of mass.

FIG. 5 is a diagram for describing determination of a pressure center direction and inferring of a location. The pressure center direction refers to a direction toward the center of pressure from the center of mass. In the pressure center path estimation step, the pressure center direction is first determined and a pressure center location is inferred by projecting in the determined direction. More specifically, first, in the pressure center direction determining step, as illustrated in FIG. 5, the pressure center direction is determined by a ratio of the horizontal acceleration $a_x$ to the sum of the vertical acceleration $a_z$ and a gravitational acceleration g and a ratio of the front-rear direction acceleration $a_y$ to the sum of the vertical acceleration $a_z$ and the gravitational acceleration g. When the pressure center direction is determined as described above, next, in the pressure center location inferring step, it is assumed that the center of mass is positioned at a height determined as a value acquired by multiplying the previously measured user's height information by a predetermined inferring constant (gain value) and the pressure center location is inferred by projecting to the ground in the direction determined in the pressure center direction determining step. Here, the inferring constant refers to a height of the center of mass according to the user's height. It is well known that the mass center of a child is generally higher in ratio than the mass center of an adult, and that the center of mass of a man is higher in ratio than the center of mass of a woman and of course, the ratio is also known. As a specific example, it is known that the center of mass of an adult male is averagely located at 55.27% of the height and in this case, the inferring constant becomes 0.5527. Thus, for example, by inputting child/adult and male/female classification information together when inputting the user's height information, an appropriate inferring constant may be selected and used for calculation.

In order to further increase the accuracy of the pressure center location thus obtained, a pressure center location correction step may be further performed, in which the pressure center location is corrected by a value acquired by multiplying the pressure center location inferred in the pressure center location inferring step by predetermined front-rear and horizontal correction constants. Here, the front-rear and horizontal correction constants are constants that may statistically match the pressure center location acquired by the projection method described above with actual front-rear and left-right direction pressure centers.

Figure 6:
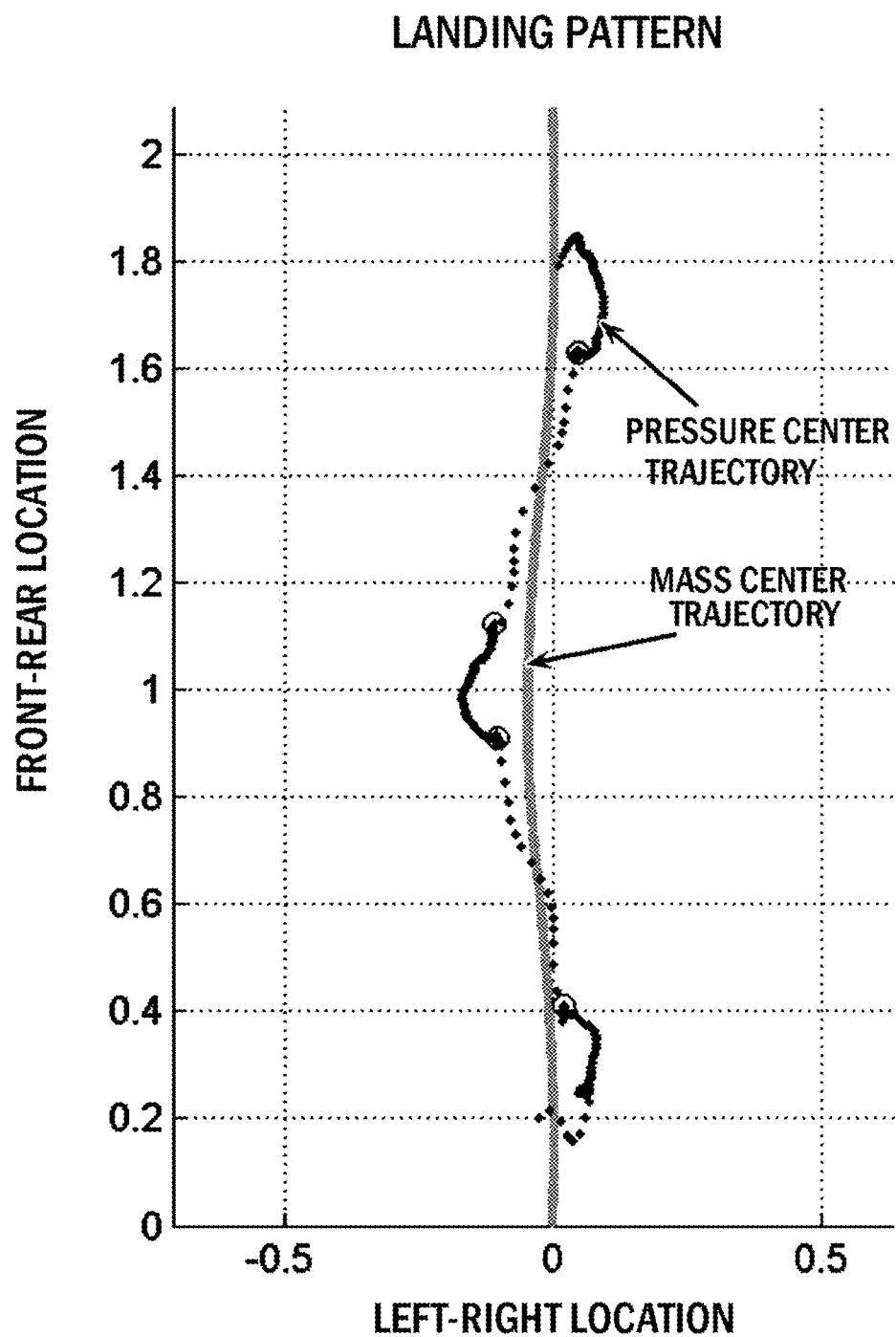

In the exercise type determining step, walking or running is determined from a pattern of a graph of the vertical acceleration $a_z$. FIG. 6 illustrates one example of a landing pattern obtained as the estimated pressure center path. As illustrated in FIG. 6 it can be known that the determination is performed while left and right feet alternately support the ground.

Figure 7A:
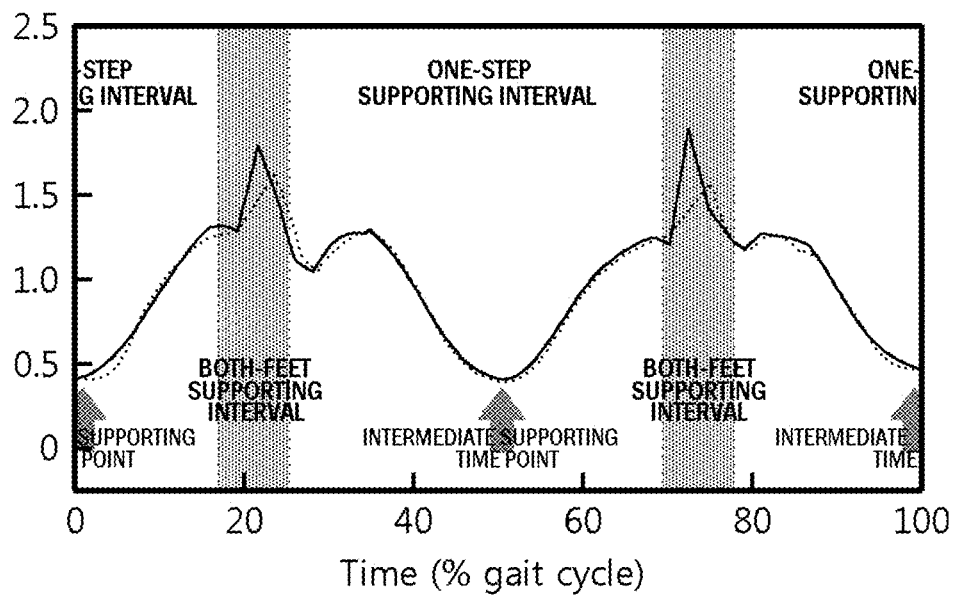
Figure 7B:
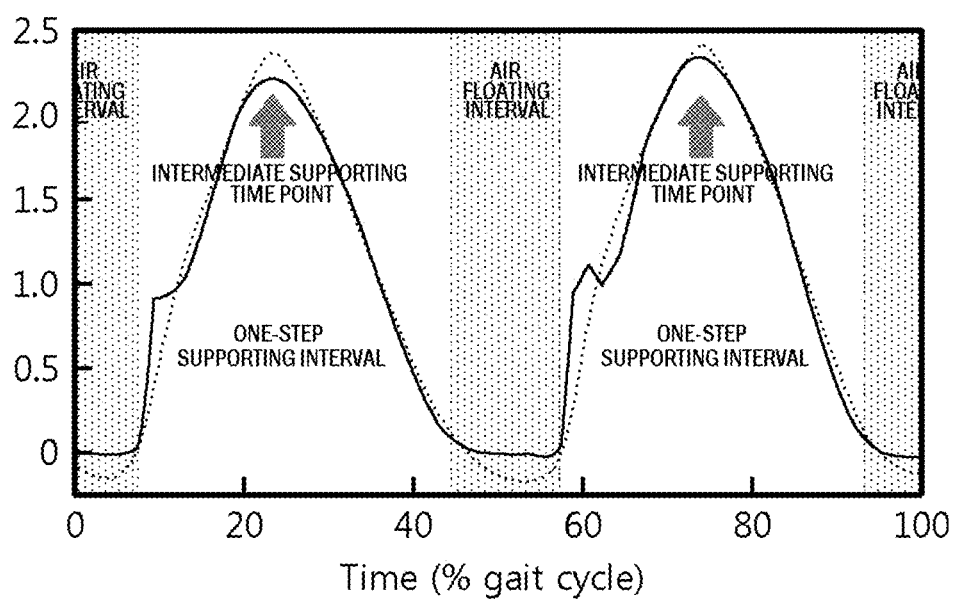

On the other hand, the distinction between the walking and the running is that one or both feet continuously touch the ground in the case of the walking, whereas one or both feet continuously float from the ground in the case of the running. FIGS. 7A-7B illustrate examples of a vertical acceleration graph with respect to time during walking and running. In the case of the graph at the time of walking illustrated in FIG. 7A, it can be seen that an instantaneous peak occurs at the moment when both feet touch the ground and in the case of the graph at the time of running illustrated in FIG. 7B, it can be seen that a constant value section exists in which an instantaneous vertical acceleration $a_z$ has a minimum value at the moment when both feet float from the ground. In this way, it is possible to determine whether the exercise of the user which is currently performed is the walking or running by using a fact that the patterns of the graph of the vertical acceleration $a_z$ are different from each other in the case of the walking and the running.

In the exercise posture deriving step, posture information is derived, which includes the stride length, the step width, the step angle, and the lateral asymmetry based on a pressure center path estimation value and the 3-axis direction accelerations $a_x$, $a_y$, and $a_z$. The present invention is described in more detail with reference to the pressure center path illustration of FIG. 6 and the vertical acceleration illustration during the walking or running of FIGS. 7A-7B.

First of all, it is described above that the cases where the exercise of the user is the walking and the running show slightly different aspects and of course, there is a case where the aspects are commonly shown. As described above, in the case of the walking, one foot or both feet continuously touch the ground and in the case of the running, one foot or both feet continuously float from the ground. That is, there is an interval that the body is supported only by one foot commonly during the walking and the running. In consideration of the points, the exercise posture driving step first is configured to include an intermediate supporting time determining step of determining an intermediate supporting time and an interval classification determining step of determining a both-feet supporting interval, a one-foot supporting interval, and an air floating interval to form basic information for deriving the posture while distinguishing the walking and the running.

First, the walking exercise is described as follows for easy understanding. First, at the moment when a heel of one foot touches the ground, the walking exercise starts a state where a toe of the other foot is not yet also dropped from the ground, that is, a state where both feet are supported. In this state, when the other foot is separated from the ground while supporting the ground with only one foot, the human body also moves forwards while the other foot moves forward while the other foot churns the air. In addition, at the moment when the heel of the other foot touches the ground, while the state where the toe of the one foot is not yet dropped from the ground, that is, the state where both feet are supported are achieved again, one-step walking is performed. In this process, at the moment when the human body moves forward while being supported by only one foot, the head of the person does not largely shake in the vertical direction (the local minimum is formed at the vertical acceleration $a_z$) and at the moment when the foot touches the ground, the human body greatly shakes vertically (a peak value is formed at the vertical acceleration $a_t$).

In other words, the walking exercise may be divided into an interval in which both feet are in a state of standing on the ground and an interval in which only one foot is in a state of standing on the ground and vertical shaking is least when only one foot stands on the ground. Such an exercise aspect is well illustrated in FIG. 7A and as illustrated in such an example, in an intermediate supporting time determining step, a local minimum in the vertical acceleration $a_z$ measured in a time region is defined as an intermediate supporting time when the exercise of the user is the walking. Further, in the interval classification determining step, when the exercise of the user is the walking, an interval in which the peak value is formed in the vertical acceleration $a_z$ measured in the time region is determined as the both-feet supporting interval and the remaining intervals are determined as the one-foot supporting interval.

Next, the running exercise is described as follows for easy understanding. First, the running exercise starts with the moment when one foot which comes forward spurts off the ground (in this moment, the other foot is floating in the air). In this state, as one foot floats by spurting off the ground, the human body moves forward while both feet float in the air, and simultaneously, while both feet churn the air, the front and the rear are changed and the other foot thus comes forward. At the same time when the other foot which comes forward touches the ground, the other foot spurts off the ground again, and as a result, one-step running is performed.

In this process, at the moment when one foot spurts off the ground, the head of the person does greatly shakes in the vertical direction (the local maximum is formed in the vertical acceleration $a_z$) and in a state where the foot goes ahead while the foot floats in the air, the head does not almost shake in the vertical direction (a constant value is formed in the vertical acceleration $a_z$).

In other words, the running exercise may be divided into an interval in which both feet are in a state of floating in the air and an interval in which only one foot is in a state of standing on the ground and vertical shaking is least when both feet float in the air. Such an exercise aspect is well illustrated in FIG. 7B and as illustrated in such an example, in an intermediate supporting time determining step, a local maximum in the vertical acceleration $a_z$ measured in a time region is defined as an intermediate supporting time when the exercise of the user is the running. Further, the interval classification determining step, when the exercise of the user is the running, an interval in which the constant value appears in the vertical acceleration $a_z$ measured in the time region is determined as an air floating interval and the remaining intervals are determined as the one-foot supporting interval. Here, the constant value appearing in the air floating interval is a predetermined value of a signal level measured by an accelerometer when any external force other than gravity is not applied, and may be appropriately determined to be a value close to approximately zero. That is, the constant value is a reference value that allows a current stance to be discriminated. Therefore, in this sense, the constant value may be called a stance phase constant and in summary, when the vertical acceleration is smaller than the stance phase constant during the running, the corresponding interval is determined as the air floating interval and when the vertical acceleration is larger than the stance phase constant, the corresponding interval is determined as the one-foot supporting interval. When base higher metrics for deriving the posture are derived as described above, it is possible to derive the walking or running posture such as the stride length, the step width, the step angle, the lateral asymmetry, or the like at last.

Stride length: First, the user location information is measured at a predetermined time interval to calculate an average speed. Next, a walking frequency is calculated by measuring the number of intermediate supporting time points during the time interval. Last, the average speed is divided by the walking frequency to accurately calculate the stride length of the user.

Step width: A horizontal step width may be calculated by using a pressure center location value corresponding to the intermediate supporting time. That is, a time value corresponding to the intermediate supporting time illustrated in FIG. 7A or FIG. 7B is applied to the pressure center location value illustrated in FIG. 6 and when the pressure center location corresponding to the time value is found, a location where the left foot stands on the ground and a location where the right foot stands on the ground are obtained and the step width of the user may be accurately calculated by measuring a space between the both locations.

Step angle: The step angle may be calculated by using a pressure center location value corresponding to a start time point of the one-foot supporting interval and a pressure center location value corresponding to an end time point of the one-foot supporting interval. For easy understanding, at the start time point of the one-foot supporting interval, the heel of the foot stands on the ground and at the end time point of the one-foot supporting interval, the toe of the foot stands on the ground. That is, as described above, obtaining an angle between the pressure center locations refers to obtaining an angle between a foot heel location and a foot toe location at the moment when the foot stands on the ground, i.e., the step angle and in other words, the step angle of the user may be accurately calculated by such a method.

Figure 8:
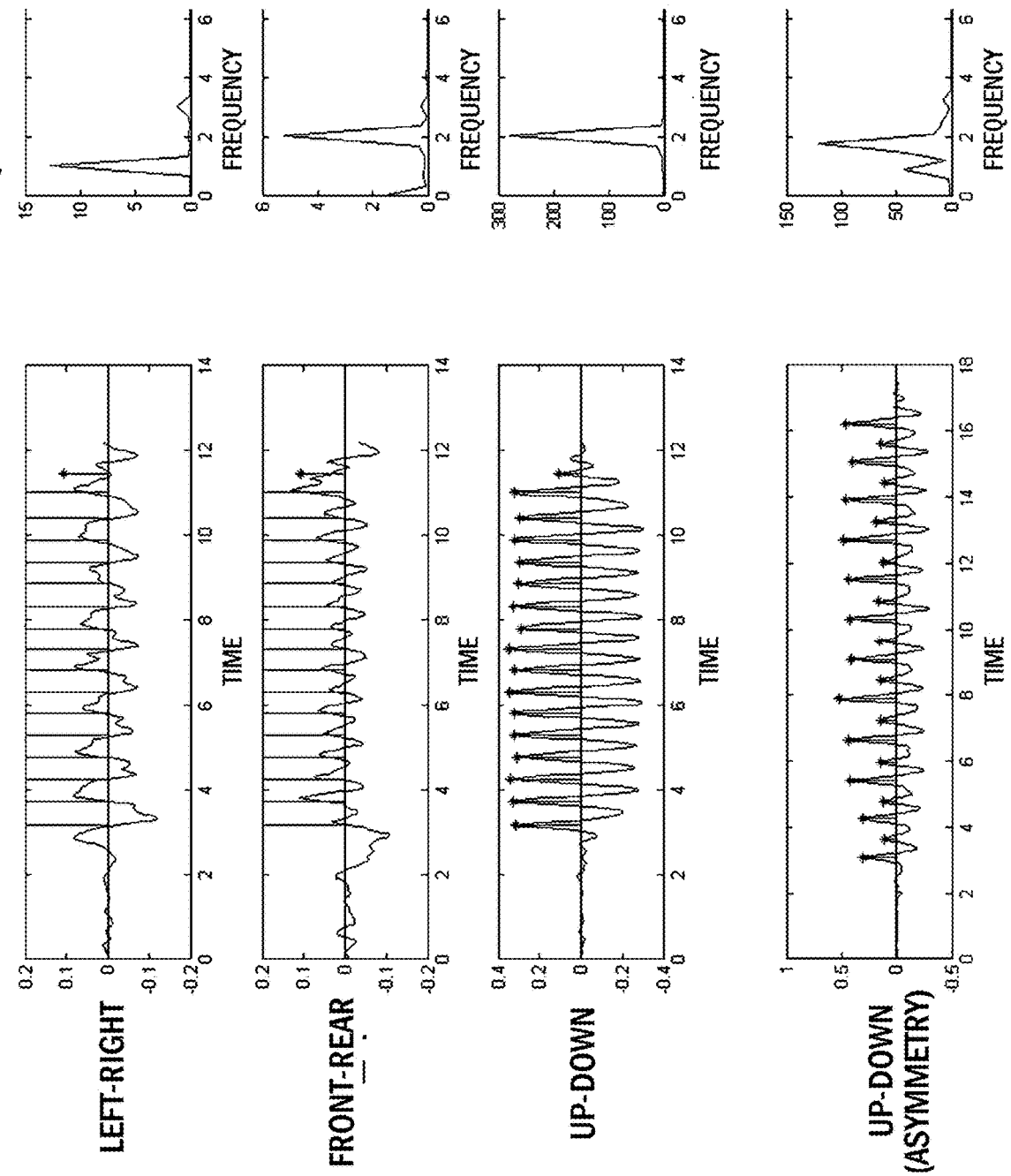

Lateral asymmetry: First, the supporting foot is identified based on a sign of the horizontal acceleration $a_x$ measured in the time region. Next, the peak value and a valley value of the vertical acceleration $a_z$, which are measured in the time region, and a difference value between the peak value and the valley value are compared. That is, the peak values, the valley values, and the like in the case where the left foot supports the human body and the right foot supports the human body are compared to accurately calculate the lateral asymmetry of the user. Further, repeatability of the walking or running may be calculated in the same manner. FIG. 8 illustrates an example of an acceleration signal measurement result and it can be seen that the lateral asymmetry of the vertical acceleration $a_z$ strongly appears in a lowermost graph of FIG. 8.

The metrics including the stride length, the step width, the step angle, the lateral asymmetry, and the like may be calculated by the aforementioned method.

Calculation Implementation Example of Injury Risk Related Metric

In relation with calculation of the injury risk related metric, first, referring to FIG. 1, the detailed configuration of the metric calculating unit 121 of the present invention is described in brief and calculation of an instantaneous vertical loading rate (IVLR) metric which is the injury risk related metric will be described below in detail.

As illustrated in FIG. 1, the metric calculating unit 121 of the present invention may basically include a high pass filter (HPF) 124 extracting a high frequency signal of a predetermined frequency or more from a collected vertical acceleration signal and a calculation unit 125 detecting a peak value between a first time point and a second time point from the high-frequency signal filtered by the high pass filter (HPF) 124, calculating an average value of the detected peak values, and calculating an estimation value of an instantaneous vertical loading rate (IVLR) by multiplying the average value by an estimation coefficient $k_1$.

In this case, the estimation coefficient value $k_1$ is determined as a regression coefficient obtained through the average value of the calculated peak values and measurement values (or values calculated through the measurement values) collected from a force plate and an infrared motion capture system and a regression analysis.

In general, the instantaneous vertical loading rate (IVLR) is very difficult to obtain from the data collected from the sensors worn by the user's body like the system. The reason is that in terms of power, when most wearable devices utilize a battery as a power source, available power is fairly limited, while the instantaneous vertical loading rate (IVLR) represents a slope value, so the instantaneous vertical loading rate (IVLR) may be precisely measured only at a high sampling rate (in general, 1000 Hz or more).

Sensors with high sampling rates are very difficult to wear on the wearable devices due to power problems. In general, sensors that may be used in mobile or wearable devices have a sampling rate of less than 200 Hz and with such a low sampling rate, the IVLR measurement accuracy is very poor.

Figure 19A:
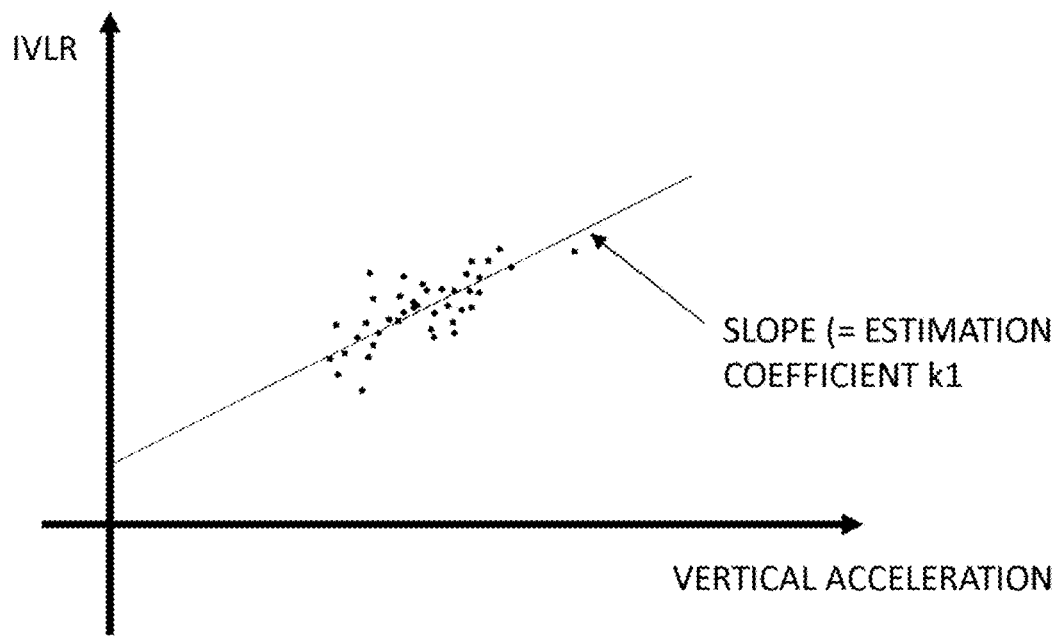
FIGS. 19A-19B are graphs for describing calculation of an instantaneous vertical load rate (IVLR) estimation coefficient according to an embodiment of the present invention.
Figure 19B:
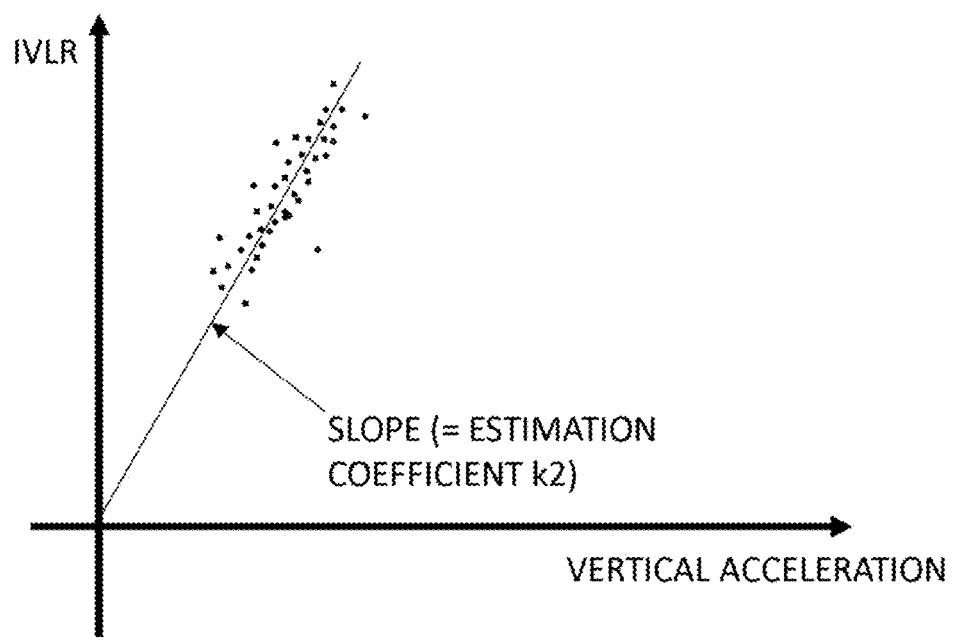

However, applicants of the present invention have found that the average value of the peak value of a high frequency component of the vertical acceleration signal or the sum of the high frequency power signal of the Fourier transform of the vertical acceleration signal among the metrics that may be collected using the sensor in the mobile device or the wearable device has a high correlation with the IVLR value through an experiment. Therefore, as illustrated in FIGS. 19A-19B, a fact that the IVLR value may be significantly precisely estimated by using estimation coefficients $k_1$ and $k_2$ obtained through the regression analysis of the average value of the IVLR and the peak value of the high frequency component of the vertical acceleration signal and the sum of the IVLR or the high frequency power signal of the Fourier transform of the vertical acceleration signal is applied to the present invention.

Here, as a unit of the IVLR, N/s which is an absolute unit representing force per time may be used or the unit of the IVLR may be expressed as g/s. Alternatively, since the sensor applied to the present invention basically collects not the force but the acceleration data, data is collected in BW/s which is a relative unit (here, BW represents Body Weight). When the acceleration data is multiplied by a mass m of the user, the acceleration data may be expressed even as N/s ((N=m*g)/s) which is the absolute unit. In this case, the mass m of the user may be included in the estimation coefficient $k_1$ or $k_2$ or calculated by the estimation coefficient $k_1$ or $k_2$ as a separate coefficient times the mass m of the user.

On the other hand, the high-frequency signal may mean, for example, an acceleration vertical signal of 10 Hz or more, which is difficult to generate an acceleration vertical signal of 5 Hz or more by a user's voluntary motion, and an acceleration vertical signal generated in a situation such as an impact is generally present in a high band, and as a result, in the present invention, the high-frequency signal of 10 Hz or more is used for estimating the instantaneous vertical loading rate (IVLR).

The calculation unit 125 detects the peak value between the first and second time points from the filtered high frequency signal, and the first time point may be, for example, a ground landing time point of the user and the second time point may be, for example, a ground reaction force peak intermediate time point. The time points will be described below with reference to FIG. 9A-9B.

Additionally, the metric calculating unit 120 may further include a frequency domain transforming unit 127 transforming the acceleration vertical signal collected by the sensor unit 111 from the time domain to a frequency domain and a power signal detection signal 126 detecting a power signal from the acceleration vertical signal in the frequency domain. In this case, the high-pass filter 124 may extract a high-frequency power signal of a predetermined frequency or more from the detected power signal and the calculation unit 125 may calculate the sum of the high-frequency power signals and calculate the estimation value of the instantaneous vertical loading rate (IVLR) by multiplying the sum of the high-frequency power signals by the estimation coefficient $k_2$.

In this case, the frequency domain transforming unit 127 may operate to convert the acceleration vertical signal from the time domain to the frequency domain by using fast Fourier transform (FFT).

On the other hand, in this case, the high-frequency power signal may mean, for example, force signals of 10 Hz or more and it is difficult to generate a force signal of 5 Hz or more by the user's voluntary motion, and the force signal generated in a situation such as the impact, etc., is generally present in the high band, and as a result, in the present invention, the instantaneous vertical loading rate (IVLR) may be estimated and calculated as the metric by using the high-frequency power signal of 10 Hz or more.

Figure 9A:
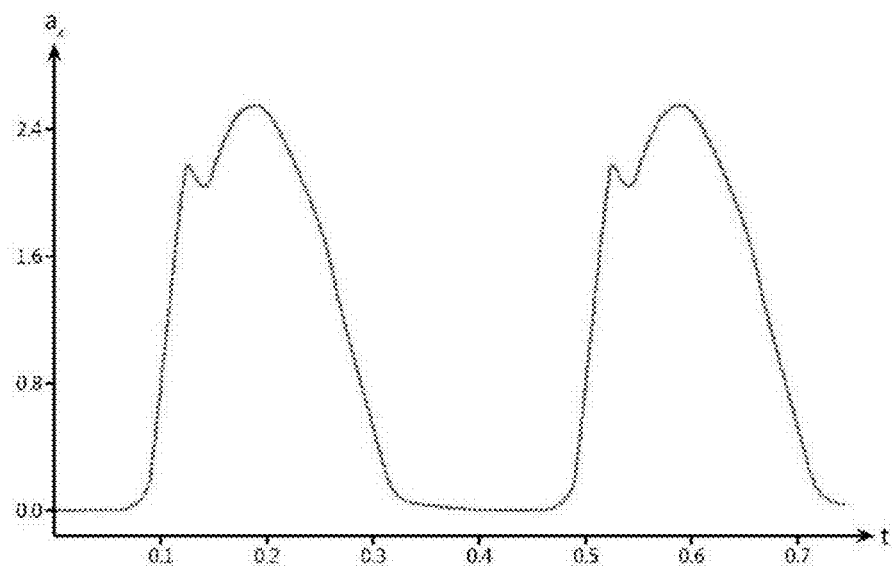
FIGS. 9A-9B, 10A-10C, and 11A-11B are diagrams for describing an embodiment of a method for calculating a metric related to an injury risk of the present invention.

Hereinafter, the calculation method of the instantaneous vertical loading rate (IVLR) will be described in detail. Prior to this, first, the graph of the vertical acceleration $a_z$ is described. FIG. 9A is a diagram showing the vertical acceleration graph during the running. As illustrated in FIG. 9A, the vertical acceleration $a_z$ appears in a periodic form with respect to the time (this is natural because the walking or running itself is periodic exercise). The running exercise is described as follows for easy understanding.

First, the running exercise starts with the moment when one foot stretched to the front spurs the ground (in this moment, the other foot is floating in the air). In this state, as one foot floats by spurring the ground, the human body moves forward while both feet float in the air, and simultaneously, while both feet churn the air, the front and the rear are changed and the other foot thus comes forward. At the same time when the other foot which comes forward touches the ground, the other foot spurts off the ground again, and as a result, one-step running is performed. In this process, at the moment when one foot stands on the ground, the head of the person greatly shakes in the vertical direction (the local maximum is formed in the vertical acceleration $a_z$) and in a state where the foot goes ahead while the foot floats in the air, the head does not almost shake in the vertical direction (a constant value is formed in the vertical acceleration $a_z$).

The most impact is applied to a joint at the moment when the foot is landed, and the impact appears in the form of a first peak in the vertical acceleration graph as illustrated in FIG. 9A. The risk of injury varies depending on the degree of impact at this time, and this is calculated as the metric to be used as a basis for quantified determination of the injury risk. As the determination metric, an average slope of the vertical acceleration $a_z$, and a maximum slope, impact force, an impulse, and the like of the vertical acceleration $a_z$ may be used.

First, when an injury risk determination index is selected as the average slope value of the vertical acceleration $a_z$, the injury risk determination index is calculated by the following equation.

(Here, $a_z$: vertical acceleration, mean: average value calculation function, i: index number, $t_i$: i-th time, $t_{i-1}$: i-1-th time, $t_c$: impact start time, $t_m$: impact end time)

The impact start time refers to a moment when the foot actually stands on the ground. This may be determined as a time point when the vertical acceleration $a_z$ exceeds a predetermined reference value (e.g., 0.3 m/s²) near 0 at a value of 0 or less. Here, a specific value of the reference value for determining the impact start time may be appropriately determined among values of 0.5 ms/s² or less as in the above-described example. The impact end time as a time when the first peak value appears may be intuitively easily verified on the graph. Index i is an index of times digitized by dividing time from the impact start time to the impact end time by n, and n may be appropriately determined as necessary.

Figure 9B:
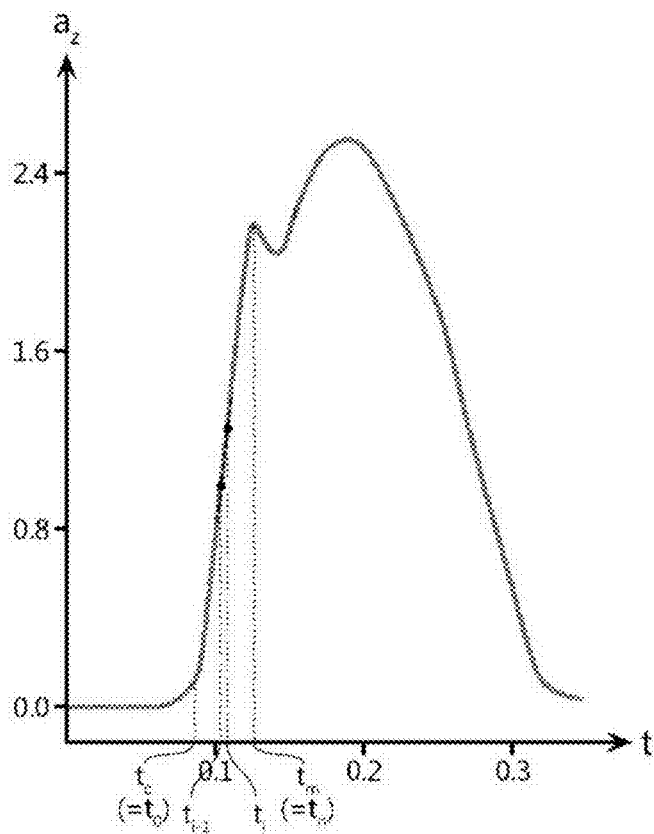
Figure 18:
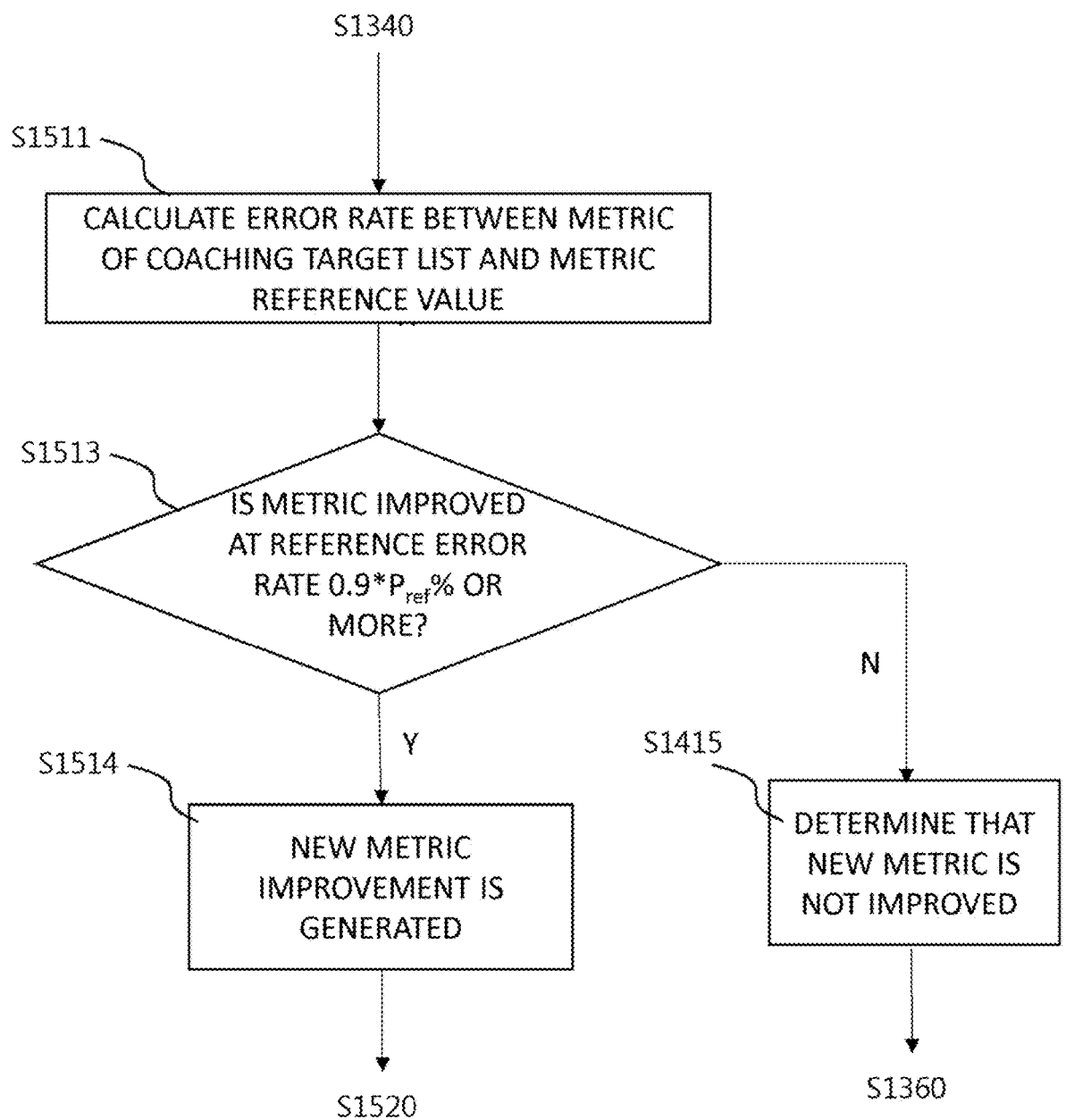
FIG. 18 is a flowchart for describing in detail a method for verifying occurrence of metric improvement of the present invention.

For example, the average slope value is thus an average value of n slope values obtained at each interval when the time from the impact start time to the impact end time is divided into n equal parts. FIG. 9B shows the graph of the vertical acceleration $a_z$ at any one period and the average slope value described above may be acquired at one period. Meanwhile, the graph of the form illustrated in FIG. 18 is continuously repeated during the running as illustrated in FIG. 9A and the average slope value described above may be acquired for each period (that is, for each step). In this case, in the determination index deriving step, an average vertical loading rate calculated by multiplying a user mass m and an average slope may be further calculated.

Meanwhile, when the injury risk determination index is selected as the maximum slope value of the vertical acceleration $a_z$, the injury risk determination index is calculated by the following equation.

$i=1, 2, \ldots, n,$ $t_0=t_c, t_n=t_m$ (Here, $a_z$: vertical acceleration, max: maximum value calculation function, i: index number, $t_i$: i-th time, $t_{i-1}$: i-1-th time, $t_c$: impact start time, $t_m$: impact end time)

The maximum slope is a maximum value among the n slope values obtained from the impact start time to the impact end time in any one period (one step) as described in the description of the average slope. In this case, in the determination index deriving step, the instantaneous vertical loading rate calculated by multiplying the user mass m and the maximum slope may be further calculated.

On the other hand, the instantaneous vertical loading rate (IVLR) may also be used as an important index for calculating the injury risk. FIG. 9B is a diagram showing the vertical acceleration graph slope during the running. Therefore, the average slope and the maximum slope of the vertical acceleration $a_z$ may be derived. In the vertical acceleration graph, the slope may correspond to the instantaneous vertical loading rate (IVLR) and the instantaneous vertical loading rate (IVLR) may be estimated by using an algorithm in the present invention.

Figure 10A:
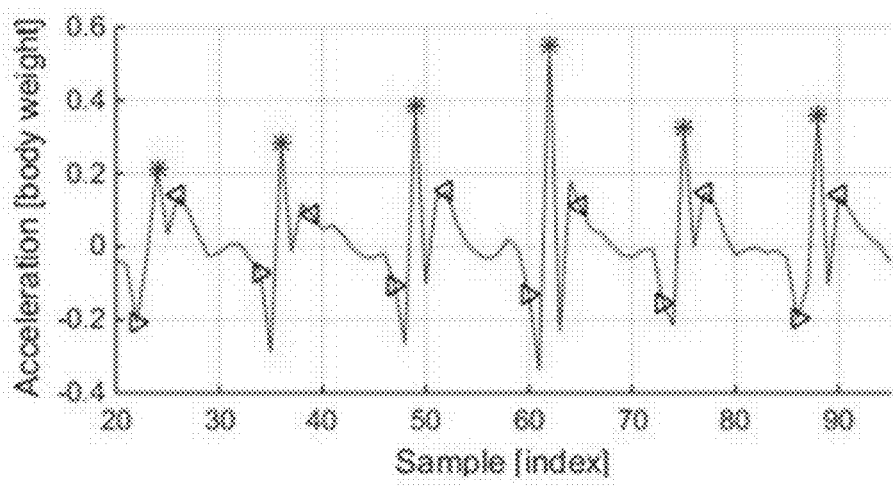
Figure 10B:
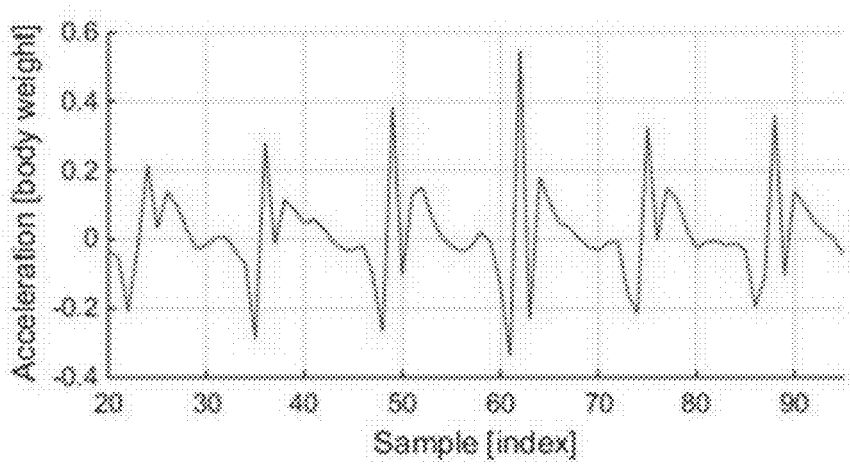
Figure 10C:
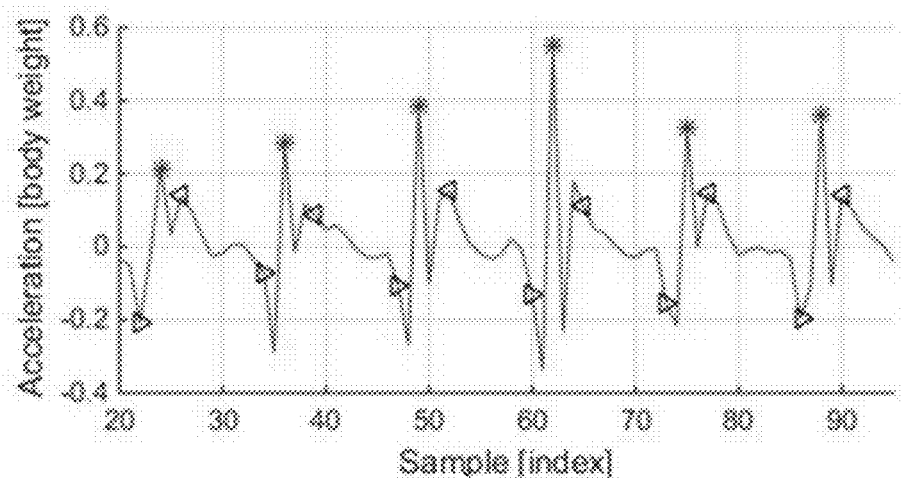

FIGS. 10A to 10C are graphs for describing calculation of an estimation value of an instantaneous vertical loading rate according to the present invention.

First, the vertical acceleration signal collected by the sensor unit 111 appears in a period form illustrated in FIG. 10A.

For the collected vertical acceleration signal, a high frequency signal of a predetermined frequency or more is extracted by filtering the collected vertical acceleration signal by using the high-pass filter 124. For example, as described above, a high frequency signal of 5 Hz or more or preferably 10 Hz or more may be extracted. FIG. 10B illustrates that the high frequency signal of 10 Hz or more is extracted from the vertical acceleration signal.

A peak value between a ground landing time point and a ground reaction force peak intermediate time point of the user is detected from the extracted high frequency signal. In FIG. 10C, the ground landing time point and the ground reaction force peak intermediate time point of the user and a peak value therebetween are illustrated.

The average value of the detected peak values is calculated and then, the average value is multiplied by the estimation coefficient $k_1$ to calculate the estimation value of the instantaneous vertical loading rate (IVLR) as the metric. The estimation value may be used as a criterion for determining the injury risk. For example, when the estimation value of the instantaneous vertical loading rate (IVLR) is larger than a predetermined value n, it may be determined that there is the injury risk.

Further, this may be used as a criterion for evaluating a correct posture (energy efficiency) and for example, when the impulse is larger than a predetermined value m, the impulse is large and mechanical energy loss is large, and as a result, it may be determined that it is inefficient. The impulse will be described below in more detail.

When the metric calculating unit 121 further includes the frequency domain transforming unit 127 and the power signal detecting unit 126, the metric calculating unit 121 may calculate the estimation value of the instantaneous vertical loading rate (IVLR) as the metric by using the power signal.

Figure 11A:
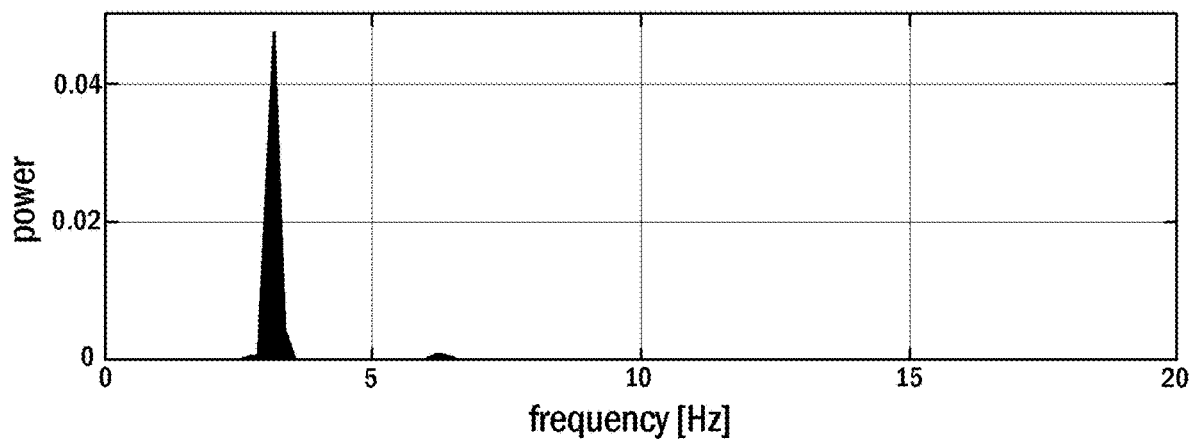

For example, the vertical acceleration signal appears in the period form illustrated in FIG. 10A. In this case, the metric calculating unit 121 converts the collected vertical acceleration signal from the time domain to the frequency domain and power (a square of FFT magnitude) which is the power signal is detected from the acceleration vertical signal in the frequency domain. FIG. 11A illustrates an example in which the acceleration vertical signal is converted into the frequency domain by using the fast Fourier transform (FFT) and the power is detected therefrom.

Figure 11B:
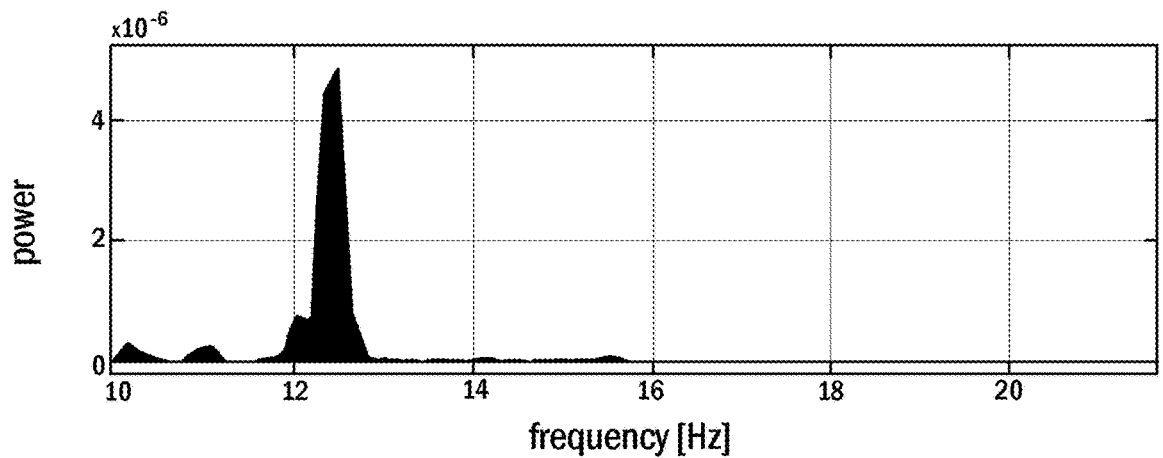

High-frequency power of a predetermined frequency or more is extracted from the detected power and the sum of the extracted high-frequency powers is calculated. For example, the high-frequency power is power of 10 Hz or more and FIG. 11B illustrates high-frequency power of 10 Hz or more.

The instantaneous vertical loading rate (IVLR) may be estimated by multiplying the sum of the high-frequency powers by the estimation coefficient $k_2$. As described above, the estimated instantaneous vertical loading rate (IVLR) may be used as the criterion for determining the injury risk. For example, when the instantaneous vertical loading rate (IVLR) is larger than a predetermined value n, it may be determined that there is the injury risk.

Further, this may be used as a criterion for evaluating a correct posture (energy efficiency) and for example, when the impulse is larger than a predetermined value m, the impulse is large and mechanical energy loss is large, and as a result, it may be determined that it is inefficient.

Figure 12:
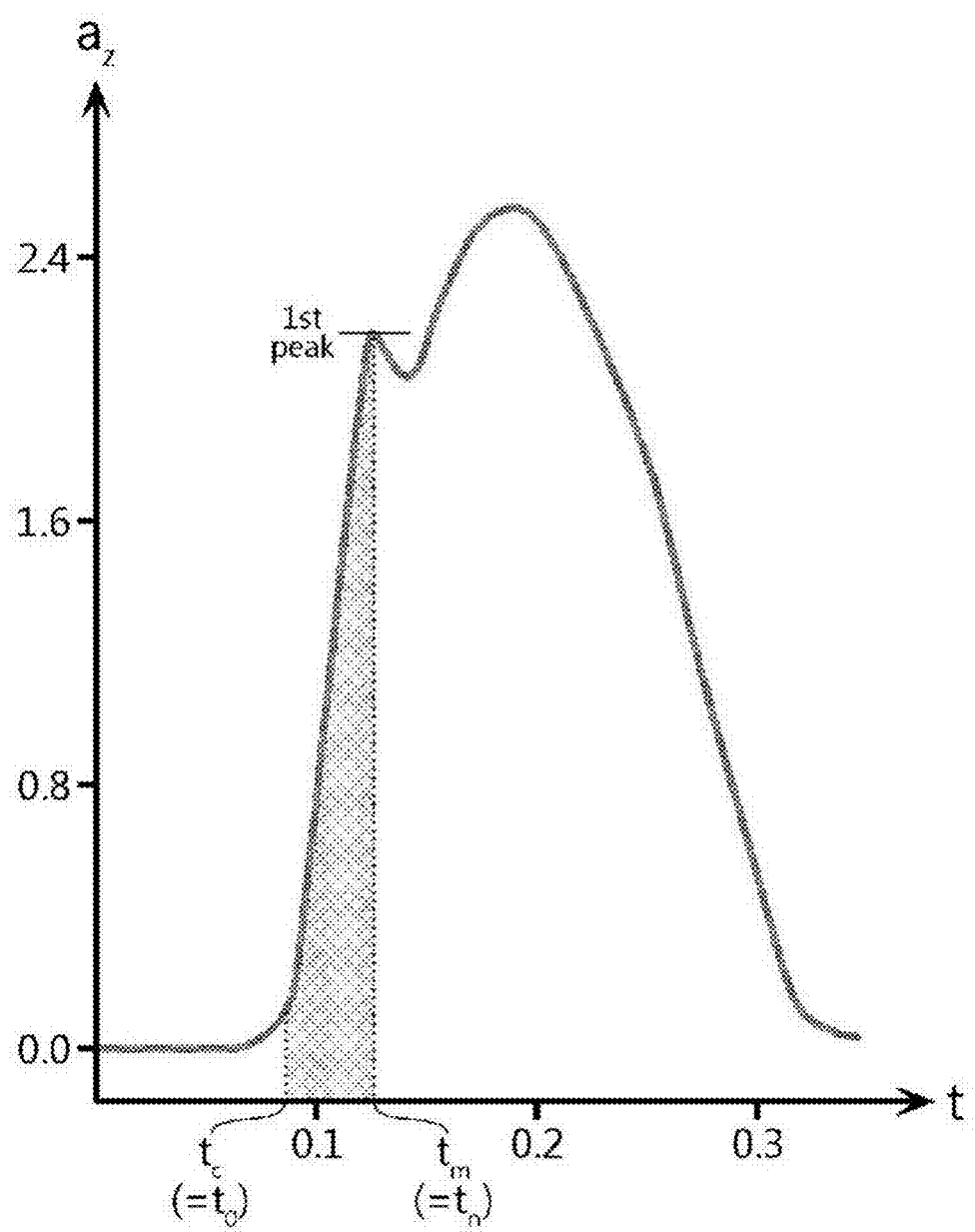
FIG. 12 is a graph showing the impulse in vertical acceleration when running.

FIG. 12 is a diagram showing the impulse in the vertical acceleration graph during the running. The value of the impact force may be calculated by using the following equation.

$$\text{Impact force} = m \times a_z(t_m)$$

(Here, $a_z$: vertical acceleration, m: user mass, $t_m$: impact end time)

Figure 16:
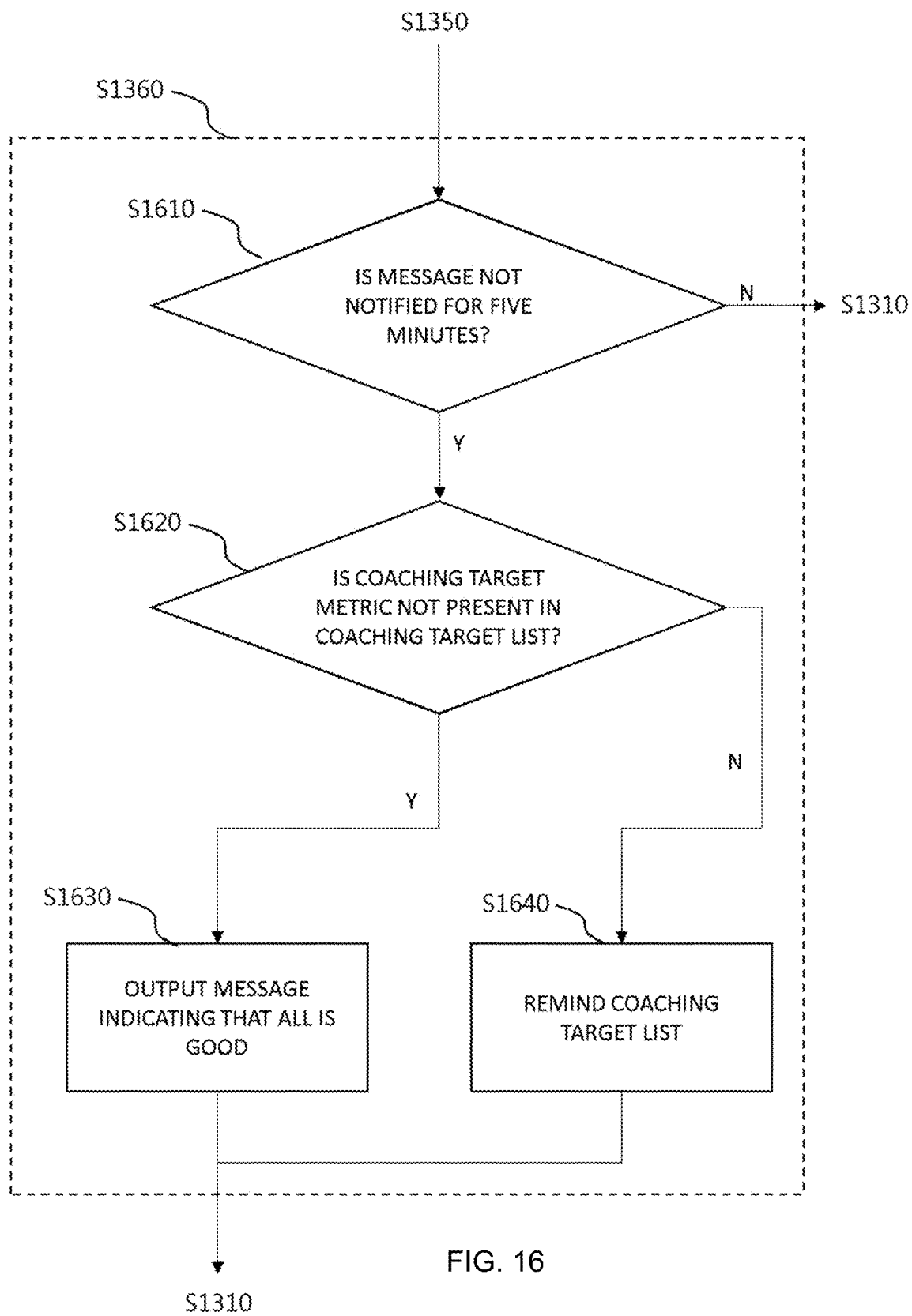
FIG. 16 is a flowchart illustrating a method for alarming a current exercise state of the present invention.

As described above, since the impact end time is the time when the first peak value appears, a time when the impact force appears becomes the impact end time, of course. In FIG. 16, the first peak of the vertical acceleration $a_z$ is illustrated and here, a value acquired by multiplying the first peak by the user mass m precisely becomes an impact force value.

Meanwhile, an impulse value may be calculated by using the following equation.

$$\text{Impulse} = m \int_{t_c}^{t_m} a_z dt$$

(Here, $a_z$: vertical acceleration, m: user mass, $t_c$: impact start time, $t_m$: impact end time)

In FIG. 12, a graph area of the vertical acceleration $a_z$ between the impact start time and the impact end time is illustrated and a value acquired by multiplying the area by the user mass m precisely becomes the impulse value.

Automatic Coaching Method Using Calculated Metric

The coaching guide generating unit 122 serves to generate coaching guide information including information on posture correction when a current walking or exercise posture needs to be corrected by using a metric value derived by the metric calculating unit 121. Here, generating the coaching guide information is a concept including at least any one of determining a coaching target metric indicating that the injury risk is high or efficiency of the exercise deteriorates due to an inappropriate walking/running posture; selecting an alarm phrase depending on the coaching target metric or a level of badness of the coaching target metric; and generating an alarm phrase including a correction amount of the coaching target metric.

Figure 13:
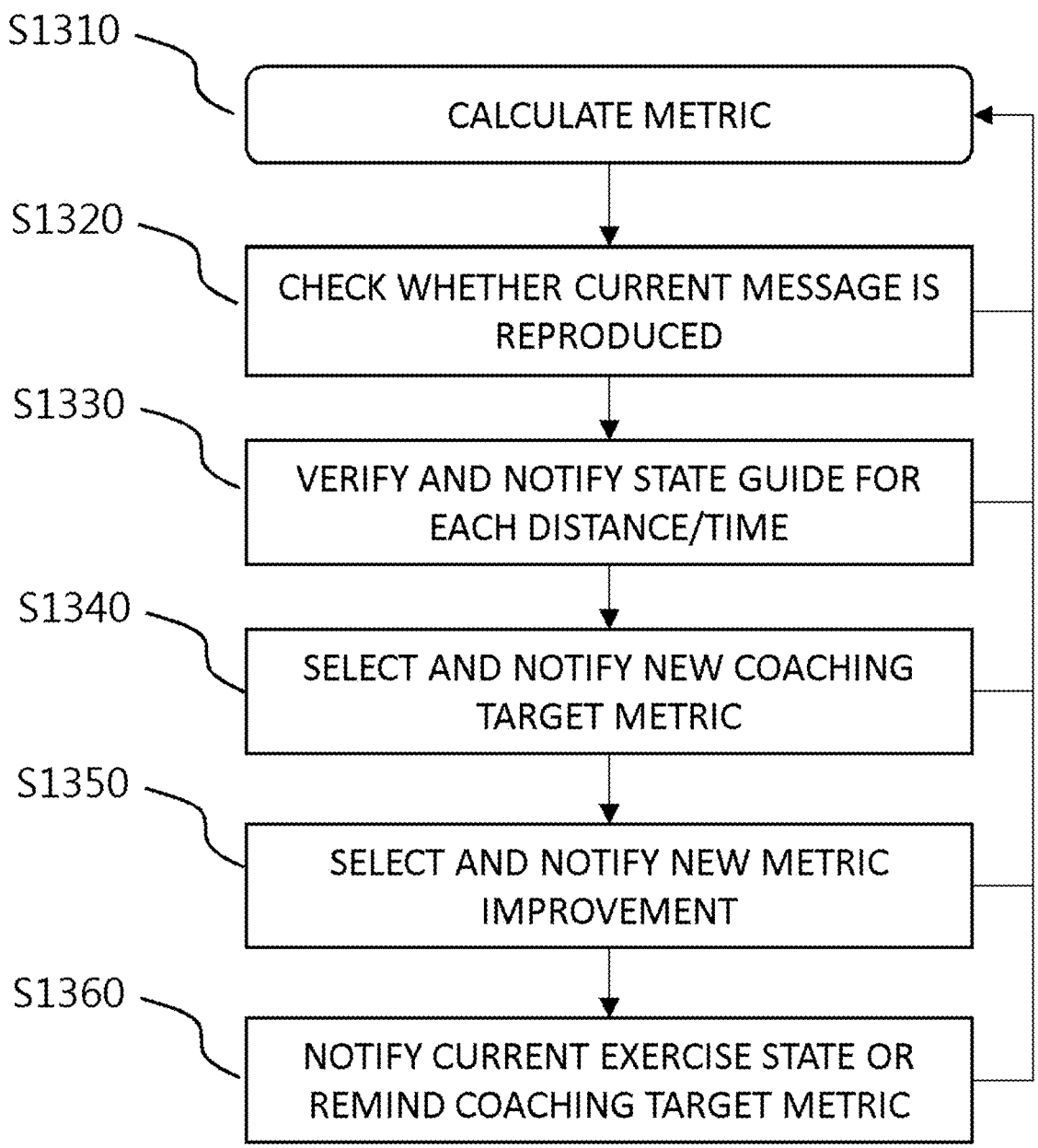
FIG. 13 is a flowchart illustrating an automatic coaching method of the present invention.

An automatic coaching operation of the coaching guide generating unit 122 is illustrated in FIG. 13.

First, the metric calculating unit 121 of the control unit 120 calculates metrics related to the exercise posture and the injury risk based on the sensor data collected by the sensor unit 111 (S1310).

After calculating the metric, it is checked whether a coaching guide message reproduced by the coaching guide output unit 130 is currently present or the coaching guide message is output within a predetermined time (S1320). In this case, when the coaching guide message being reproduced is present or the coaching guide message is output within the predetermined time, the metric calculating step (S1310) is repeated again.

Next, the coaching guide generating unit 122 checks whether the current operation is a coaching guide operation within a predetermined state guide period (S1330). In this case, the coaching guide generating unit 122 may set a state guide period so as to guide a state every predetermined distance or every predetermined time based on the distance or time. For example, the coaching guide generating unit 122 may brief summary information of states including an exercise distance, a coaching target reminder, an exercise time, and the like every 500 or 1000 m when taking exercise through the coaching guide output unit 130.

Next, the coaching guide generating unit 122 selects a new coaching target metric (S1340). A selection algorithm of the new coaching target metric will be described below.

Next, the coaching guide generating unit 122 selects a new metric improvement (S1350). That is, it is checked whether the exercise posture of the user is improved. A specific method of the new metric improvement selection will be described below in detail in describing FIG. 15.

Last, the coaching guide generating unit 122 reports a current state when whether the new coaching target metric is generated and a coaching target new release metric are confirmed and there is no message alarm for a reference time or more. For example, in reporting the current state, there is coaching target metric, and as a result, the exercise may be performed in the correct posture or a coaching target list is not improved, and as a result, the coaching target list may be reminded.

Selection of New Coaching Target Metric and Alarm

Figure 14:
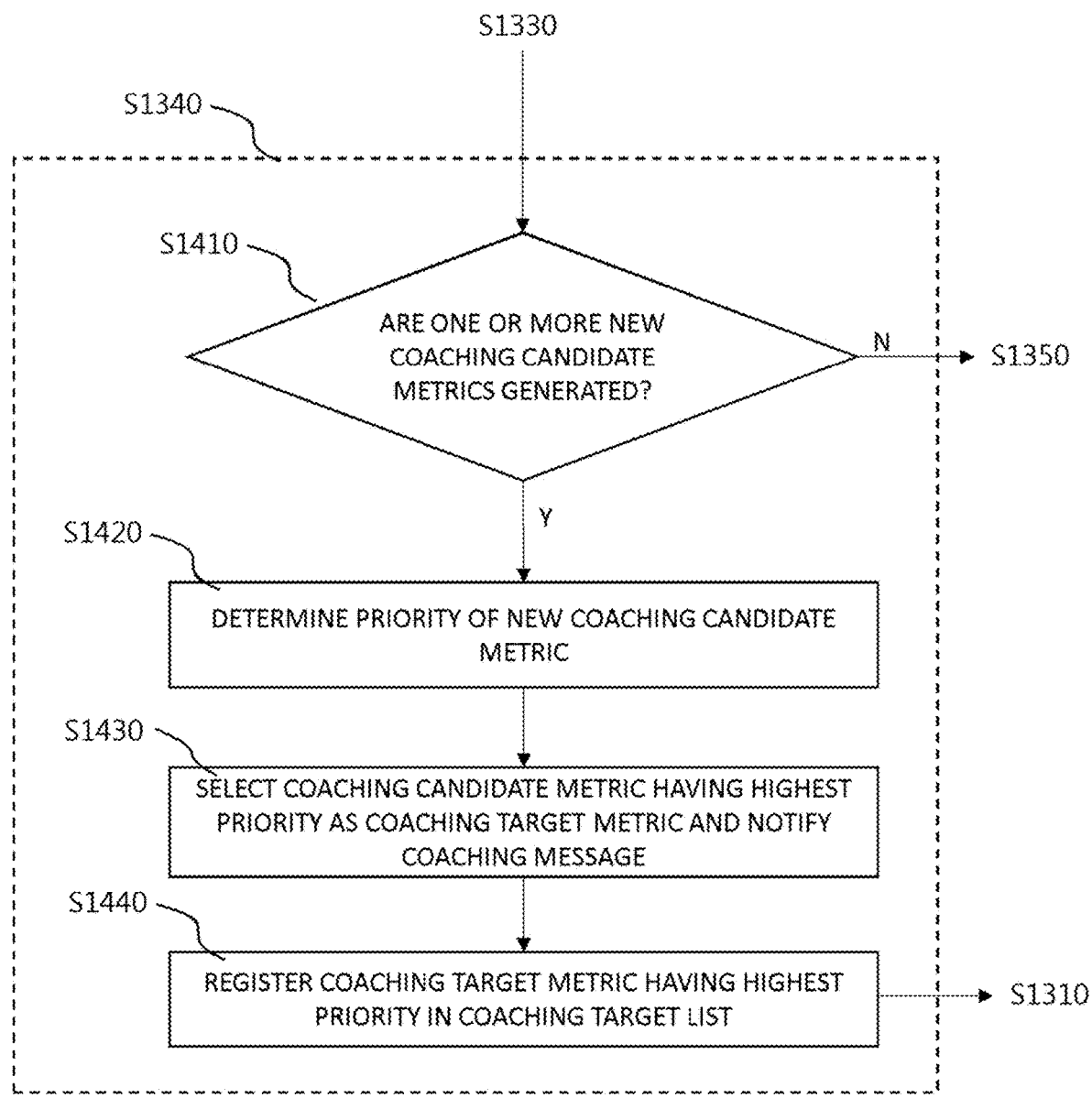
FIG. 14 is a flowchart illustrating a method for verifying generation of a new coaching target metric and alarming a metric having a high priority of the present invention.

Hereinafter, with reference to FIGS. 14 and 17, the new coaching target metric selection will be described in detail. FIG. 14 is a flowchart of a new coaching target metric selecting step and FIG. 17 is a flowchart of a step of checking whether a new coaching candidate metric is generated.

First, the coaching guide generating unit 122 performs a state guide period coaching guide confirming operation (S1330) and thereafter, checks whether a new coaching candidate metric is generated for selecting the new coaching target metric (S1410).

Figure 17:
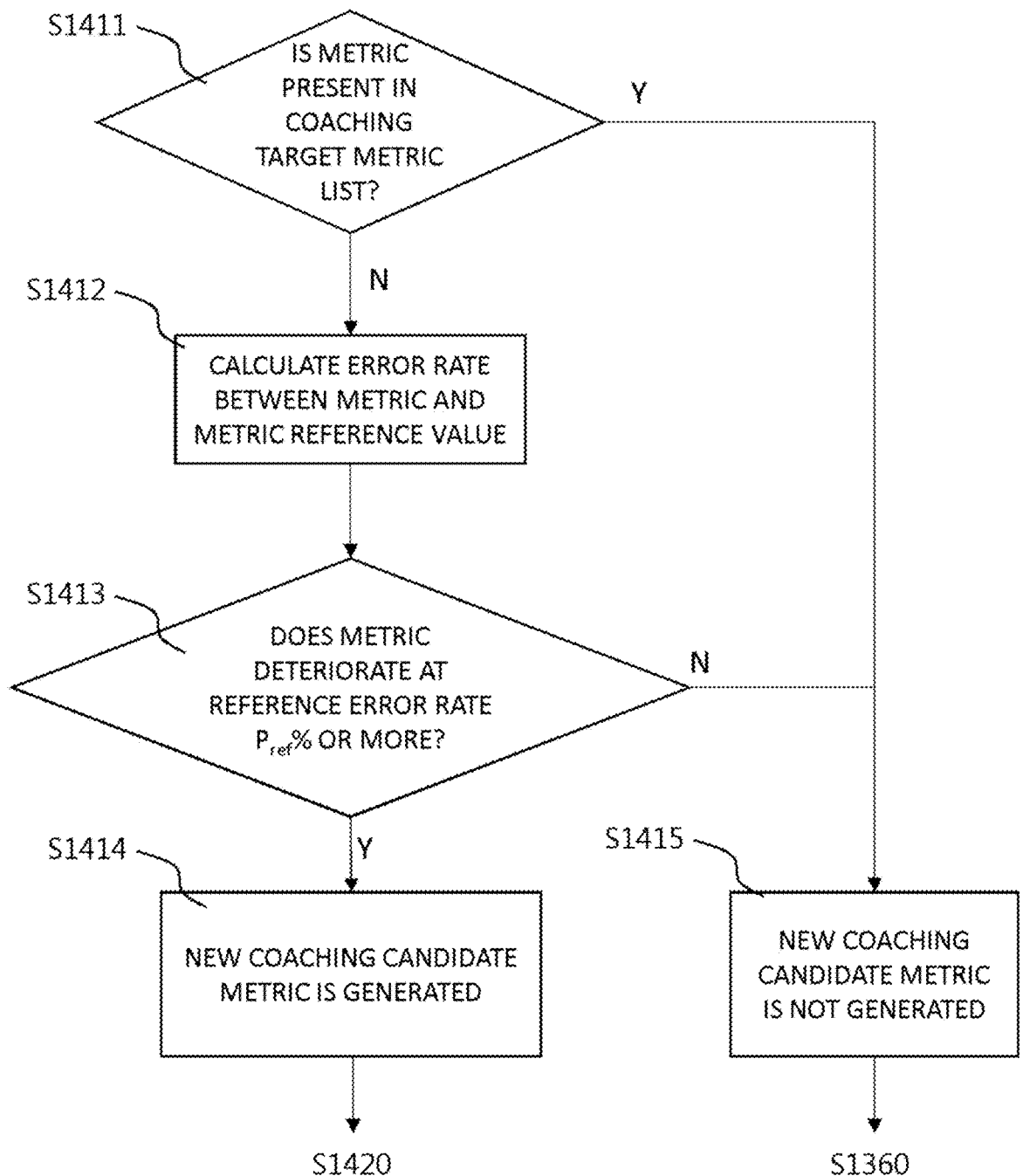
FIG. 17 is a flowchart illustrating in detail a method for verifying generation of a new coaching target metric of the present invention.

More specifically, referring to FIG. 17, the coaching guide generating unit 122 first checks whether a metric to be reviewed is in the coaching target list (S1411). Here, for example, the coaching target list as a list storing a metric in which the coaching guide message is output for a predetermined period is a list which becomes a reference to determine improvement or deterioration of the metrics.

When the metric is not present in the coaching target list, a difference between the corresponding metric and a metric reference value is acquired and an error rate is acquired (S1412). The error rate P is acquired as in Equation 1 below when the corresponding metric is denoted by $X_i$ and the metric reference value is denoted by $M_{ref}$.

$$P=(M_{ref}-X_i)/M_{ref} \quad \text{(Equation 1)}$$

In this case, the metric reference value is stored in advance in the coaching guide generating unit 122. For example, the coaching guide generating unit 122 may store optimum height-stride length relationship data for each walking and running speed as a reference value of the stride length metric. Alternatively, a reference value of an instantaneous vertical loading rate metric according to a height and/or weight may be stored.

Meanwhile, the error rate P is compared with a reference error rate $P_{ref}$ and it is check whether the corresponding metric deteriorates at the reference error rate or more (S1413).

In this case, a determination criterion related to whether the corresponding metric deteriorates may be changed for each metric. For example, when the impulse metric or the IVLR metric is increased, the user's body is overloaded, so that the increase of the metric value means deterioration. As another example, the stride length or step width metric may have a reference range having an upper limit and a lower limit, and may be determined to be deteriorated when the stride length or step width metric is out of the reference range. Last, in the case of the metric such as the lateral balance, when the corresponding metric value is smaller than a metric reference value, it may be determined that the corresponding metric deteriorates.

When the corresponding metric deteriorates at the reference error rate $P_{ref}$ or more, it is determined that a new coaching candidate metric is generated (S1414) and otherwise, it is determined that the new coaching candidate metric is not generated.

Referring back to FIG. 14, when the new coaching candidate metric is generated, a priority of the new coaching candidate metric is determined (S1420). However, when the new coaching candidate metric is not generated, the process proceeds to the new metric improvement selection step (S1350).

Meanwhile, the priority is determined according to the magnitude and frequency of the error rate. For example, when the new coaching candidate metric is generated, it is first determined whether the metric is coached to a reference number of times (n) or less for reference time. That is, when a coaching guide frequency of the new coaching candidate metric is equal to or less than the reference number of times, the error rate p of the metric is multiplied by a weight value $W_i$ per metric to determine a priority $K_i$.

$$K_i=p*W_i \quad \text{(Equation 2)}$$

In this case, when the coaching guide frequency of the new coaching candidate metric is equal to or more than the reference number of times (n times), the corresponding metric is excluded from the new coaching candidate metric. The reason is that when the alarm for the corresponding metric is excessively generated, the user feels inconvenience and the awareness of the metric is reduced, which hinders efficient exercise. Therefore, the reference number of times is appropriately controlled to reduce inconvenience in the user experience.

The weight per metric is an element set because the weight has different importance for each metric. For example, the weight of the metric representing the risk of injury may be set to a high value, and the weight of the metric representing the exercise posture may be set to be relatively low compared to the weight of the injury risk related metric.

Therefore, according to the present invention, only when an important exercise metric deteriorates while a frequent alarm reduces the inconvenience of the user, the alarm may be notified, thereby remarkably increasing the efficiency of the exercise.

After the priority $K_i$ is determined, the metric having the highest priority among the new coaching candidate metrics is selected as the new coaching target metric, and the coaching message for the selected metric is output through the coaching guide output unit 130 (S1430). A user interface such as a display or a voice alarm which may be used during the exercise, such as a mobile phone or a wearable device may present only significantly limited information to the user. Therefore, the coaching alarm is performed only for the metric having the highest priority.

On the other hand, after the coaching alarm, the coaching candidate metric having the highest priority is registered in the coaching target list (S1440). The coaching target list is used as a basic data for saving an alarm history and reducing the fatigue of the user due to repeated alarms. In addition, the process returns to the metric calculating step (S1310) again to repeat the overall operation.

Checking Whether Metric is Improved

Figure 15:
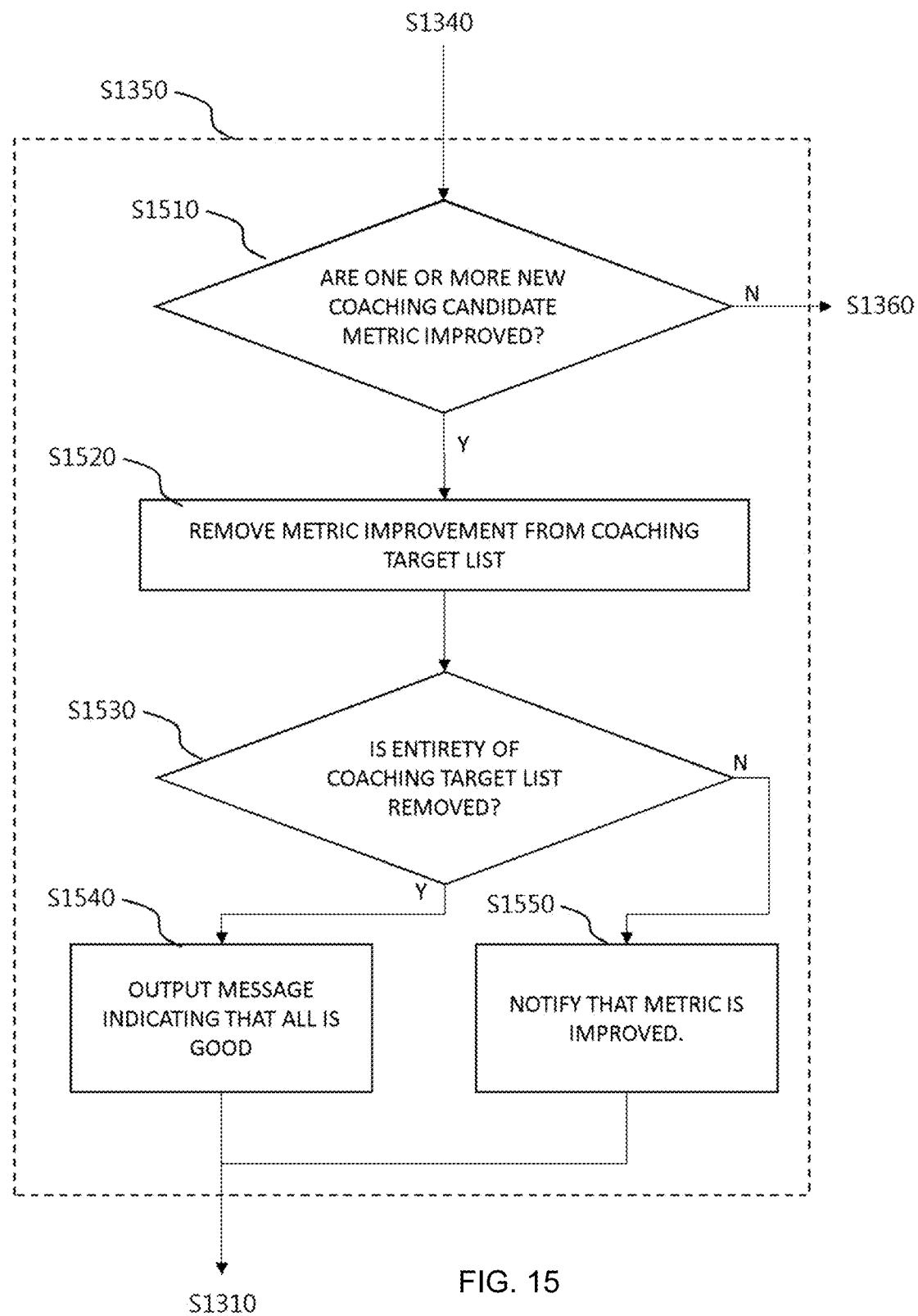
FIG. 15 is a flowchart for describing a method for verifying occurrence of metric improvement and alarming metric improvement of the present invention.

Hereinafter, referring to FIGS. 15 and 18, a method for checking whether the new metric is improved will be described in detail. FIG. 15 is a flowchart of a step of checking whether a new metric is improved.

First, the coaching guide generating unit 122 checks whether the new metric is improved after checking whether the new coaching target metric is generated (S1340) (S1510).

More specifically, referring to FIG. 18, the coaching guide generating unit 122 first checks the error rates of the metrics in the coaching target list (S1511). Since the calculation of the error rate is the same as the calculation of the error rate at the time of discrimination of the new coaching target metric, the description is omitted. The calculated error rate P of the metrics in the coaching target list is compared with the improvement criterion error rate $P_{refi}$. Preferably, the improvement reference error rate $P_{refi}$ is set different (e.g., smaller than) from the reference error rate $P_{ref}$ when selecting the new coaching target metric. For example, the improvement reference error rate $P_{refi}$ is set at a level of 85 to 95% of the reference error rate $(P_{ref})$ at the time of selecting the new coaching target metric.

The reason for differently setting the improvement reference error rate and the deterioration reference error rate is as follows. When a certain metric is collected at a value that is close to the reference error rate, the metric value may repeatedly exceed or fall below the reference error rate. In this case, the corresponding metric may be repeatedly classified as unnecessary improvement and deterioration and may be classified as improvement is achieved even though the metric is not reliably improved. Therefore, by setting the reference deterioration reference error rate to be 5 to 15% higher than the improvement reference error rate, the state of the metric is set to be improved after the improvement for the corresponding metric is surely achieved.

Meanwhile, the coaching guide generating unit 122 checks whether the corresponding metric is improved with respect to the improvement reference error rate as a result of the comparison (S1513).

In this case, a determination criterion related to whether the corresponding metric is improved may be changed for each metric. For example, the reduction of the impulse metric or the instantaneous vertical loading rate (IVLR) metric means improvement. As another example, the stride length or step width metric may have a reference range having an upper limit and a lower limit, and may be determined to be improved when a deviation of the stride length or step width metric from the reference range is reduced. Last, in the case of the metric such as the lateral balance, it may be determined that the corresponding metric is improved when the corresponding metric value is larger than a metric reference value.

When the corresponding metric is improved at the improvement reference error rate Prefi or more, it is determined that the new metric is improved (S1514) and otherwise, it is determined that the new metric is not improved (S1515).

Referring back to FIG. 15, when the new metric is improved, the corresponding improved metric is removed from the coaching target list (S1520). In addition, it is checked whether the entirety of the coaching target list is removed (S1530).

In this case, when the entirety of the coaching target list is removed, an alarm message indicating that all metrics are good is output through the coaching guide output unit 130. When the entirety of the coaching target list is not removed, the alarm message indicating that the corresponding metric is improved is output through the coaching guide output unit 130 only for the improved metric and the process returns to the metric calculating step (S1310) again to repeat the overall operation.

Last, referring to FIG. 16, a current exercise state notification step will be described in detail. FIG. 16 is a flowchart of a current exercise state notification step.

When the new coaching target metric and the metric improvement are not newly selected as the previous steps, the process proceeds to the current exercise state notification step (S1360) which is a last step.

First, the coaching guide generating unit 122 checks whether there is no message notification for a reference time (for example, five minutes) when the new coaching target metric and the metric improvement do not newly occur (S1610). In this case, when there is no notification for the reference time, the process returns to the metric calculating step (S1310) to repeat the overall operation.

However, when there is the notification for the reference time, it is checked whether there is a coaching target metric in the coaching target list (S1620).

In this case, when there is no coaching target list, an alarm message indicating that all metrics are good is output through the coaching guide output unit 130 (S1630). When the coaching target list still remains, an alarm message for reminding at least some of the metrics in the coaching target list is output through the coaching guide output unit 130 (S1640). After all processes end, the process returns to the metric calculating step (S1310) again to repeat the overall operation.

Therefore, according to the present invention, there is a big effect that by using equipment that can be easily carried and which can be easily worn on the body such as the head, waist, etc., the general person can receive coaching for an exercise posture by himself/herself or can easily measure the risk of injury during running.

Further, in terms of a device configuration, according to the present invention, there is a great advantage that only a sensor measuring a dynamic physical quantity of a user can be used such as an acceleration sensor. Therefore, effects such as the enhancement of user convenience and the economic enhancement of each user or producer may also be obtained through the great advantage.

Further, from the viewpoint of the user experience, when an alarm is given too frequently for coaching, the user may feel uncomfortable and the alarm may greatly affect efficient exercise. Therefore, an automatic coaching system of the present invention can preferentially correct an exercise posture which is most important and is to be urgently improved.

Figure 20:
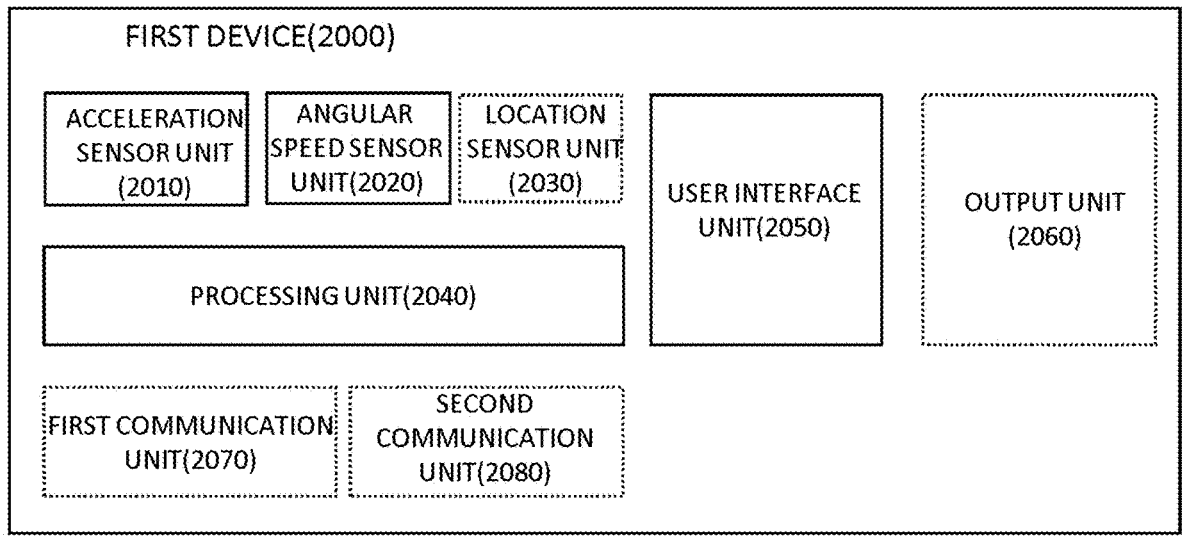
FIG. 20 illustrates a first exercise recognition device according to an embodiment of the present invention.

FIG. 20 illustrates a first exercise recognition device according to another embodiment of the present invention.

The first exercise recognition device (hereinafter, referred to as a first device) 2000 according to the embodiment includes an acceleration sensor unit 2010, an angular speed sensor unit 2020, a processing unit 2040, and a user interface unit 2050. The first device 2000 according to the embodiment is worn on the body of the user and measures a dynamic physical quantity of the user, such as an acceleration and an angular speed to analyze exercise states of the user, such as walking and running. As in an example illustrated in FIG. 1, the first device 2000 may be formed in a band worn on the head and the waist, a form attached to the head and the waist in a clip type, a form provided on a hat, a form put in a belt, a glasses form, a helmet form, a form attached to the ear, a form attached to clothes, and a form worn by using a separate vest or harness. Specifically, the glasses form may be formed in a form such as augmented reality (AR) glasses, an eyeglass frame, sunglasses, or the like. The form attached to the ear may be formed in forms such as hands-free earpiece, a headphone, and the earphone. Besides, it is apparent to those skilled in the art that the first device 2000 may be formed in variously modified forms. The first device 2000 may be formed on one substrate in the form of an integrated circuit capable of performing various calculations.

The acceleration sensor unit 2010 measures 3-axis direction acceleration values including up and down, right and left, and front and rear.

The angular speed sensor unit 2020 measures 3-axis direction angular speed values including up and down, right and left, and front and rear.

The processing unit 2040 generates a first exercise state value based on the 3-axis direction acceleration values and the 3-axis direction angular speed values. The first exercise state value is at least one of an exercise time, an exercise step number, a cadence, a stride length, a step angle, a head angle, a ground support time, an air floating time, a ratio of ground supporting time to air floating time, maximum vertical force, an average vertical loading rate, a maximum vertical loading rate, lateral symmetry, and lateral stability. The first device 2000 may determine the exercise state of the user through the first exercise state value. Referring to a meaning of each first exercise state value, the cadence represents the number of steps per minute, the step width represents an average of intervals of the legs, the step angle represents an average of leg angles, the head angle represents an average of upper and lower head angles, the ground supporting time represents a supporting time when the leg touches the ground, the air floating time represents an average of times when all legs do not touch the ground, the maximum vertical force represents a maximum value of ground reaction force, the average vertical loading rate represents an average of initial slopes of supporting sections of left and right ground reaction forces, and the maximum vertical loading rate represents a maximum value of the initial slope of the supporting sections of the left and the right ground reaction force.

The lateral stability means whether the exercise states are maintained in the respective legs of the left and foot and the right foot in time, force, etc. and is denoted by % by using a variation coefficient of each leg and acquired through the following equations.

Stability(Left)=1−std(Left indices)/mean(Left indices)

Stability(Right)=1−std(Right indices)/mean(Right indices)

Values which may be used as an index which is an evaluation index include a maximum vertical force value, a maximum vertical acceleration value, stance time impulse, a supporting time, a floating time, the instantaneous vertical loading rate, and the average vertical loading rate.

The left-right balance represents a left-right unbalance (%) and is acquired through the following equation.

Balance=Left index/(Left index+Right index)*100%

The user interface unit 2050 controls a sleep mode or an alive mode of the processing unit 2040. The user interface unit 2050 may be implemented in a software or hardware form. For example, the user interface unit 2050 may be implemented as a push button which is the software or hardware form. A flowchart of the exercise recognition method initiated from a user input of the user interface unit 2050 will be described below in detail in FIG. 22.

Meanwhile, the first device 2000 according to the embodiment may further include a first communication unit 2070. The first communication unit 2070 transmits the first exercise state value to a second device 2100. The first communication unit 2070 may transmit the first exercise state value to the second device 2100 at a predetermined period and it is apparent to those skilled in the art that the transmission may be implemented in various transmission schemes. The second device 2100 according to the embodiment may be various types of devices such as a computer, a mobile terminal, a clock, and the like.

Meanwhile, the first device 2000 according to the embodiment may further include a second communication unit 2080. The second communication unit 2080 transmits the first exercise state value (metric value) to a server 2200.

Meanwhile, the first device 2000 according to the embodiment may further include a location sensor unit 2030.

The location sensor unit 2030 measures a user location value. It is apparent to those skilled in the art that the location sensor unit 2030 measures the user location value based on a GPS, or ultra-precise GPS navigation technology, but may use other techniques.

When the first device 2000 further includes the location sensor unit 2030, the processing unit 2040 generates a second exercise state value based on at least one value of the first exercise state value, the user location value, and a user profile. The second exercise state value is at least one of an exercise distance, an exercise speed, calorie consumption, an altitude, and the stride length. Referring to the meaning of each second exercise state value, the altitude means a vertical height at which the body moves during the exercise and the stride length means a distance at which the body advances and moves during the ground supporting interval and the air floating interval. The user profile includes personal information such as a height, a weight, and the like of the user.

Further, the processing unit 2040 may additionally generate posture correction information by selectively comparing at least one of the first exercise state value and the second exercise state value with each predetermined reference value. For example, the processing unit 2040 stores optimal height-stride length relationship data for each exercise speed and determines whether the stride length is not excessively wide or narrow relative to the user's height based on the stride length among the second exercise state values. The processing unit 2040 generates a stride length correction amount to be decreased or increased as the posture correction information when the stride length deviates from an optimal range.

Meanwhile, the first device 2000 according to the embodiment may further include an output unit 2060. The output unit 2060 converts the posture correction information into information which may be recognized by the user, which is at least one of sound, illustration, image, and vibration and outputs the converted information. For example, when the stride length correction amount is calculated and the stride length needs to be reduced, a voice such as "Reduce the stride length." is output or an alarm sound is output through a speaker to induce the user to recognize that the stride length is not an optimal stride length and change a walking posture. Alternatively, the first device 2000 is connected to an external device such as the mobile terminal, the clock, the computer, and a dedicated display so that correction information is output to at least one of sound, illustration, image, and vibration.

When the first device 2000 further includes the location sensor unit 2030, the first device 2000 may further include a third communication unit that transmits the second exercise state value to the server 2200. The server 2200 accumulates and stores the second exercise state value in a database. The server 2200 provides statistical data based on the second exercise state value stored in the database. The statistical data includes a maximum value, a minimum value, and an average value for each second exercise state value with respect to a predetermined exercise interval. A user who needs to analyze the exercise may receive the statistical data through the server 2200 and variously utilize the received statistical data for improvement of his or her exercise habit. A user who needs to analyze the exercise may be an ordinary person walking or jogging daily to promote health or an expert trained to improve a physical ability. Further, the server 2200 stores the second exercise state value for each user and provides a big data service to analyze the second exercise state value relationally and statistically.

It is apparent to those skilled in the art that the first communication unit 2070, the second communication unit 2080, and the third communication unit are configured by at least one of wireless communication including Bluetooth, WiFi, and NFC and wired communication through wiring, but other wired/wireless communication technology may be used. Further, the first communication unit 2070, the second communication unit 2080, and the third communication unit may be physically configured by a single interface or configured by a plurality of interfaces.

Figure 21:
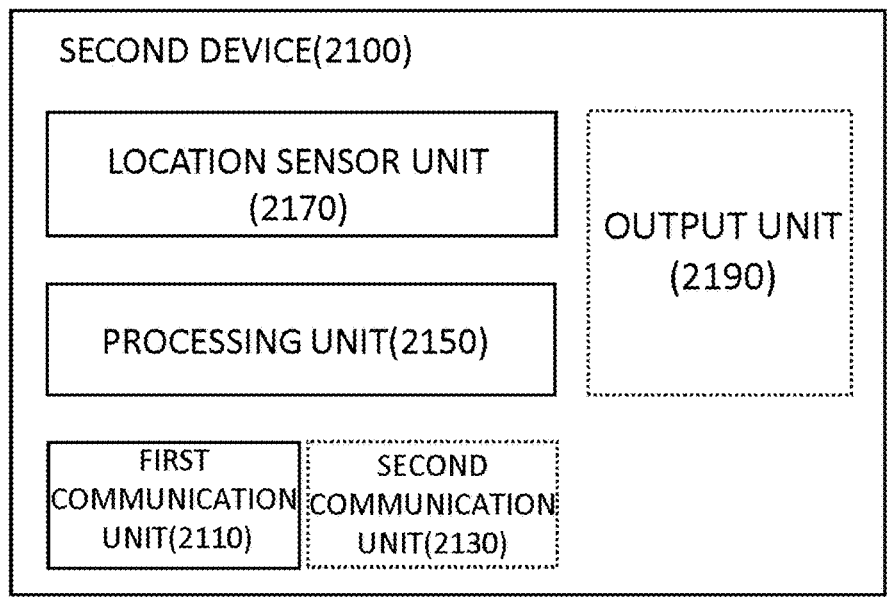
FIG. 21 illustrates a second exercise recognition device according to an embodiment of the present invention.

FIG. 21 illustrates a second exercise recognition device according to yet another embodiment of the present invention.

The second exercise recognition device (hereinafter, referred to as a second device) 2100 according to the embodiment includes a first communication unit 2110, a processing unit 2150, and a location sensor unit 2170. The second device 2100 according to the embodiment may be various types of devices such as a computer, a mobile terminal, a clock, and the like.

The first communication unit 2110 receives from the first device 2000 the first exercise state value generated based on the 3-axis direction acceleration values and the 3-axis direction angular speed values.

The location sensor unit 2170 measures the user location value. It is apparent to those skilled in the art that the location sensor unit 2030 measures the user location value based on a GPS, or ultra-precise GPS navigation technology, but may use other techniques.

The processing unit 2150 generates the second exercise state value based on at least one value of the first exercise state value, the user location value, and the user profile. The second exercise state value is at least one of a distance, a speed, calorie consumption, an altitude, and the stride length. The user profile includes personal information such as a height, a weight, and the like of the user.

Meanwhile, the processing unit 2150 according to the embodiment may additionally generate exercise posture correction information by selectively comparing at least one of the first exercise state value and the second exercise state value with each predetermined reference value. For example, the processing unit 2150 stores optimal height-stride length relationship data for each exercise speed and determines whether the stride length is not excessively wide or narrow relative to the user's height based on the stride length among the second exercise state values. The processing unit 2150 generates a stride length correction amount to be decreased or increased as the posture correction information when the stride length deviates from an optimal range.

Meanwhile, the second device 2100 according to the embodiment may further include an output unit 2190. The output unit 2190 converts the posture correction information into information which may be recognized by the user, which is at least one of sound, illustration, image, and vibration and outputs the converted information. For example, when the stride length correction amount is calculated and the stride length needs to be reduced, a voice such as "Reduce the stride length." is output or an alarm sound is output through a speaker to induce the user to recognize that the stride length is not an optimal stride length and change a walking posture.

Meanwhile, the second device 2100 according to the embodiment may further include a second communication unit 2150. The second communication unit 2150 transmits the second exercise state value to the server 2200. The server 2200 accumulates and stores the second exercise state value in a database. The server 2200 provides statistical data based on the second exercise state value stored in the database. The statistical data includes a maximum value, a minimum value, and an average value for each second exercise state value with respect to a predetermined exercise interval. A user who needs to analyze the exercise may receive the statistical data through the server 2200 and variously utilize the received statistical data for improvement of his or her exercise habit. Further, the server 2200 stores the second exercise state value for each user and provides a big data service to analyze the second exercise state value between the users relationally and statistically.

It is apparent to those skilled in the art that the first communication unit 2110 and the second communication unit 2130 are configured by at least one of wireless communication including Bluetooth, WiFi, and NFC and wired communication through wiring, but other wired/wireless communication technology may be used. Further, the first communication unit 2110 and the second communication unit 2130 may be physically configured by a single interface or configured by a plurality of interfaces.

Figure 22:
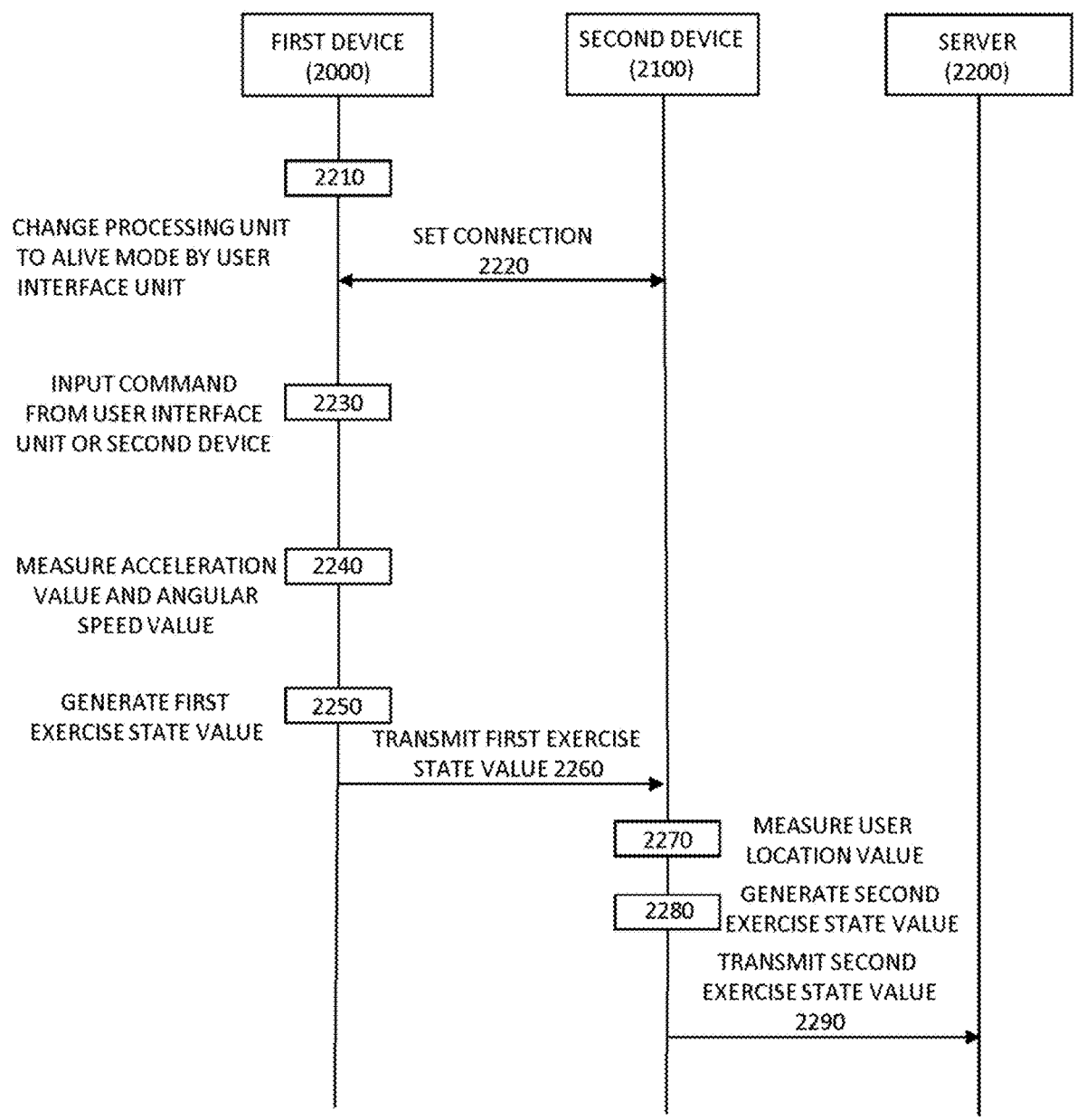
FIG. 22 is a flowchart of an exercise recognition method according to an embodiment of the present invention.

FIG. 22 is a flowchart of an exercise recognition method according to still yet another embodiment of the present invention.

In step 2210, the user interface unit 2050 of the first device 2000 changes the processing unit 2040 to the alive mode.

In step 2220, the first device 2000 sets a connection with the second device 2100 through the first communication unit 2070.

When the connection with the second device 2100 is set, the first device 2000 receives an input of a command from the user interface unit 2050 or the second device 2100 in step 2230.

In step 2240, the first device 2000 measures the 3-axis direction acceleration value and the 3-axis direction angular speed value through the acceleration sensor unit 2010 and the angular speed sensor unit 2020, respectively based on the command. According to an embodiment of the present invention, the acceleration sensor unit 2010 and the angular speed sensor unit 2020 store the 3-axis direction acceleration value in a first in first out (FIFO) queue. When a storage space of the FIFO queue is less than a predetermined threshold value, the first device 2000 changes the processing unit 2040 to the sleep mode and when the storage space of the FIFO queue is equal to or more than the predetermined threshold value, the first device 2000 changes the processing unit 2040 to the alive mode to drive the device with low power.

In step 2250, the first device 2000 generates the first exercise state value based on the 3-axis direction acceleration value and the 3-axis direction angular speed value. The first exercise state value is at least one of an exercise time, an exercise step number, a cadence, a step width, a step angle, a head angle, a ground support time, an air floating time, a ratio of ground supporting time to air floating time, maximum vertical force, an average vertical loading rate, an instantaneous vertical loading rate, lateral symmetry, and lateral stability.

In step 2260, the first device 2000 transmits the first exercise state value to the second device 2100.

In step 2270, the second device 2100 measures the user location value.

In step 2280, the second device 2100 generates the second exercise state value based on at least one value of the first exercise state value, the user location value, and the user profile. The second exercise state value is at least one of a distance, a speed, calorie consumption, an altitude, and the stride length. The user profile includes personal information such as a height, a weight, and the like of the user.

The second device 2100 may additionally generate exercise posture correction information by selectively comparing at least one of the first exercise state value and the second exercise state value with each predetermined reference value. For example, the second device 2100 stores optimal height-stride length relationship data for each exercise speed and determines whether the stride length is not excessively wide or narrow relative to the user's height based on the stride length among the second exercise state values. The second device 2100 generates a stride length correction amount to be decreased or increased as the posture correction information when the stride length deviates from an optimal range. The second device 2100 converts the posture correction information into information which may be recognized by the user, which is at least one of sound, illustration, image, and vibration and outputs the converted information. For example, when the stride length correction amount is calculated and the stride length needs to be reduced, a voice such as "Reduce the stride length." is output or an alarm sound is output through a speaker to induce the user to recognize that the stride length is not an optimal stride length and change a walking posture.

In step 2290, the second device 2100 transmits the second exercise state value to the server 2200. The server 2200 accumulates and stores the second exercise state value in a database. The server 2200 provides statistical data based on the second exercise state value stored in the database. The statistical data includes a maximum value, a minimum value, and an average value for each second exercise state value with respect to a predetermined exercise interval. A user who needs to analyze the exercise may receive the statistical data through the server 2200 and variously utilize the received statistical data for improvement of his or her exercise habit. Further, the server 2200 stores the second exercise state value for each user and provides a big data service to analyze the second exercise state value between the users relationally and statistically.

Although the preferred embodiments of the present invention have been described in detail, the scope of the present invention is not limited thereto, and various modifications and other equivalent embodiments are possible. Accordingly, the true technical scope of the present invention should be defined by the appended claims.

For example, a device according to an exemplary embodiment of the present invention may include a bus coupled to each unit of the device illustrated in the figures and at least one processor coupled to the bus and may include a memory coupled to the bus for storing a command, a received message, or a generated message and coupled to at least one processor for performing the commands described above.

Further, the system according to the present invention may be implemented as a computer readable code in a computer readable recording medium. The computer readable recording medium includes all kinds of recording devices storing data which may be deciphered by a computer system. The computer readable recording medium includes magnetic storage media (e.g., a ROM, a floppy disk, a hard disk, and the like) and optical reading media (e.g., a CD-ROM, a DVD, and the like). Further, the computer readable recording media may store and execute codes which may be distributed in the computer system connected through a network and read by a computer in a distribution method.

It is to be understood that the above-described embodiments are to be considered in all respects as illustrative and not restrictive, the scope of the present invention being indicated by the appended claims rather than by the foregoing detailed description. In addition, it should be analyzed intended that all changes and modifications that are derived from the meanings and ranges of the claims and concepts equivalents thereto are included within the scope of the present invention.

The present invention may be embodied in other specific forms without departing from its spirit or essential characteristics. The described embodiments are to be considered in all respects only as illustrative and not restrictive. The scope of the invention, therefore, will be indicated by claims rather than by the foregoing description. All changes, which come within the meaning and range of equivalency of the claims, are to be embraced within their scope.

What is claimed is:

1. A first device comprising:
an acceleration sensor unit measuring 3-axis direction acceleration values including up and down, right and left, and front and rear;
a processing unit generating a first exercise state value based on the 3-axis direction acceleration values; and
a user interface unit controlling a sleep mode or an alive mode of the processing unit;
wherein the first device is positioned on a user's body other than on or proximate the user's foot
wherein the 3-axis direction acceleration values include a vertical acceleration $a_z$, front-rear direction acceleration $a_y$, and horizontal acceleration $a_x$,
wherein the processing unit generates the first exercise state value based on a ground reaction force and a pressure center path estimated from a center of pressure, and the ground reaction force and center of pressure is calculated based on the ratio of the horizontal acceleration $a_x$ to the sum of the vertical acceleration $a_z$ and a gravitational acceleration g, and
wherein the pressure center path is estimated by a pressure center location inferred by projecting to the ground in a pressure center direction assuming that a user's mass center is located at the height calculated by multiplying a predetermined gain value by user's height.

2. The first device of claim 1, further comprising:
a first communication unit transmitting the first exercise state value to a second device.

3. The first device of claim 2, wherein the first communication unit is configured by at least one of Bluetooth, WiFi, and NFC.

4. The first device of claim 1, further comprising:
a second communication unit transmitting the first exercise state value to a server.

5. The first device of claim 1, further comprising:
a location sensor unit measuring a user location value.

6. The first device of claim 5, wherein the processing unit generates a second exercise state value based on at least one value of the first exercise state value, the user location value, and a user profile.

7. The first device of claim 6, further comprising:
a third communication unit transmitting to the server at least one of the first exercise state value and the second exercise state value.

8. The first device of claim 6, wherein the second exercise state value is at least one of a distance, a speed, calorie consumption, an altitude, and a stride length.

9. The first device of claim 6, wherein the processing unit generates posture correction information by comparing at least one of the first exercise state value and the second exercise state value with predetermined reference values.

10. The first device of claim 9, further comprising:
an output unit outputting the posture correction information by at least one of sound, illustration, video, and vibration.

11. The first device of claim 2, wherein when the processing unit is changed to the alive mode by the user interface unit,
the processing unit sets a connection with the second device through the first communication unit, and
the acceleration sensor unit generates each of the 3-axis direction acceleration values based on a command from the second device or the user interface unit.

12. The first device of claim 1, wherein the acceleration sensor unit stores the 3-axis direction acceleration values in a first in first out (FIFO) queue, and when a storage space of the FIFO queue is less than a predetermined threshold value, the processing unit is in the sleep mode and when the storage space of the FIFO queue is equal to or more than the predetermined threshold value, the processing unit is in the alive mode.

13. The first device of claim 1, wherein the first exercise state value is at least one of an exercise time, an exercise step number, a cadence, a step width, a step angle, a head angle, a ground support time, an air floating time, a ratio of ground supporting time to air floating time, maximum vertical force, an average vertical loading rate, an instantaneous vertical loading rate, lateral symmetry, and lateral stability.

14. The first device of claim 1, wherein the first device is formed in one of a band worn on the head and the waist, a form attached to the head and the waist in a clip type manner, a form provided on a hat, a form put in a belt, a glasses form, a helmet form, a form attached to an ear, a form attached to clothes, and a form worn as the clothes.

15. The first device of claim 14, wherein the glasses form is configured to be one of augmented reality glass, an eyeglass frame, and sunglasses,
the form attached to the ear is configured by one of a hands-free earpiece, a headphone, and an earphone, and
the form worn as the clothes is configured by one of a vest and a harness.

* * * * *